(12) United States Patent
Wodnicki et al.

(10) Patent No.: US 11,134,918 B2
(45) Date of Patent: Oct. 5, 2021

(54) MODULAR PIEZOELECTRIC SENSOR ARRAY WITH CO-INTEGRATED ELECTRONICS AND BEAMFORMING CHANNELS

(71) Applicants: University of Southern California, Los Angeles, CA (US); THE REGENTS OF THE UNIVERSITY OF CALIFORNIA, Oakland, CA (US)

(72) Inventors: Robert G. Wodnicki, Los Angeles, CA (US); Qifa Zhou, Arcadia, CA (US); Thomas Matthew Cummins, Venice, CA (US); Douglas N. Stephens, Davis, CA (US); Katherine W. Ferrara, Davis, CA (US)

(73) Assignees: University of Southern California, Los Angeles, CA (US); The Regents of the University of California, Oakland, CA (US)

( * ) Notice: Subject to any disclaimer, the term of this patent is extended or adjusted under 35 U.S.C. 154(b) by 474 days.

(21) Appl. No.: 15/999,109

(22) PCT Filed: Feb. 18, 2017

(86) PCT No.: PCT/US2017/018537
§ 371 (c)(1),
(2) Date: Aug. 17, 2018

(87) PCT Pub. No.: WO2017/143307
PCT Pub. Date: Aug. 24, 2017

(65) Prior Publication Data
US 2020/0046320 A1 Feb. 13, 2020

Related U.S. Application Data

(60) Provisional application No. 62/297,008, filed on Feb. 18, 2016.

(51) Int. Cl.
*A61B 8/00* (2006.01)
*B06B 1/06* (2006.01)
(Continued)

(52) U.S. Cl.
CPC .......... *A61B 8/4488* (2013.01); *B06B 1/0622* (2013.01); *H01L 41/04* (2013.01); *H01L 41/1132* (2013.01)

(58) Field of Classification Search
None
See application file for complete search history.

(56) References Cited

U.S. PATENT DOCUMENTS 4,825,115 A   4/1989   Kawabe et al.
5,398,691 A * 3/1995   Martin ................ A61B 1/0052
                                                         600/437
(Continued)

FOREIGN PATENT DOCUMENTS

WO      2015/142764 A1    9/2015

OTHER PUBLICATIONS

International Application No. PCT/US2017/018537, International Search Report and Written Opinion dated Jun. 16, 2017, 14 pages.
(Continued)

*Primary Examiner* — Katherine L Fernandez
(74) *Attorney, Agent, or Firm* — Kilpatrick Townsend & Stockton LLP

(57) ABSTRACT

A modular array includes modular array includes one or more array modules. Each array module includes one or more transducer arrays, where each of the one or more transducer arrays includes a plurality of piezoelectric elements; a conducting interposer arranged and configured to provide acoustic absorbing backing for the one or more transducer arrays; and one or more Application Specific Integrated Circuits (ASICs). The conducting interposer and
(Continued)

the one or more ASICs are in electrical contact with each other at a first direct electrical interface. Additionally, the conducting interposer and the one or more transducer arrays are in electrical contact with each other at a second direct electrical interface.

20 Claims, 14 Drawing Sheets

(51) Int. Cl.
*H01L 41/04* (2006.01)
*H01L 41/113* (2006.01)

(56) References Cited

U.S. PATENT DOCUMENTS

| | | |
|---|---|---|
| 5,638,612 A | 6/1997 | Donzis |
| 2005/0257953 A1 | 11/2005 | Walter et al. |
| 2010/0156243 A1 | 6/2010 | Weekamp et al. |
| 2010/0317972 A1 | 12/2010 | Baumgartner et al. |
| 2011/0254151 A1 | 10/2011 | Lin et al. |
| 2012/0143060 A1 | 6/2012 | Weekamp et al. |
| 2013/0257224 A1 | 10/2013 | Wodnicki et al. |
| 2013/0315035 A1 | 11/2013 | Tai |
| 2016/0151043 A1* | 6/2016 | Gu .................. A61B 8/4494 600/459 |
| 2016/0282455 A1* | 9/2016 | Scarsella .............. G01S 7/5208 |
| 2016/0296975 A1* | 10/2016 | Lukacs ................ B06B 1/0685 |

OTHER PUBLICATIONS

International Application No. PCT/US20147/018537, International Search Report dated Jun. 16, 2017, 4 pages.

* cited by examiner

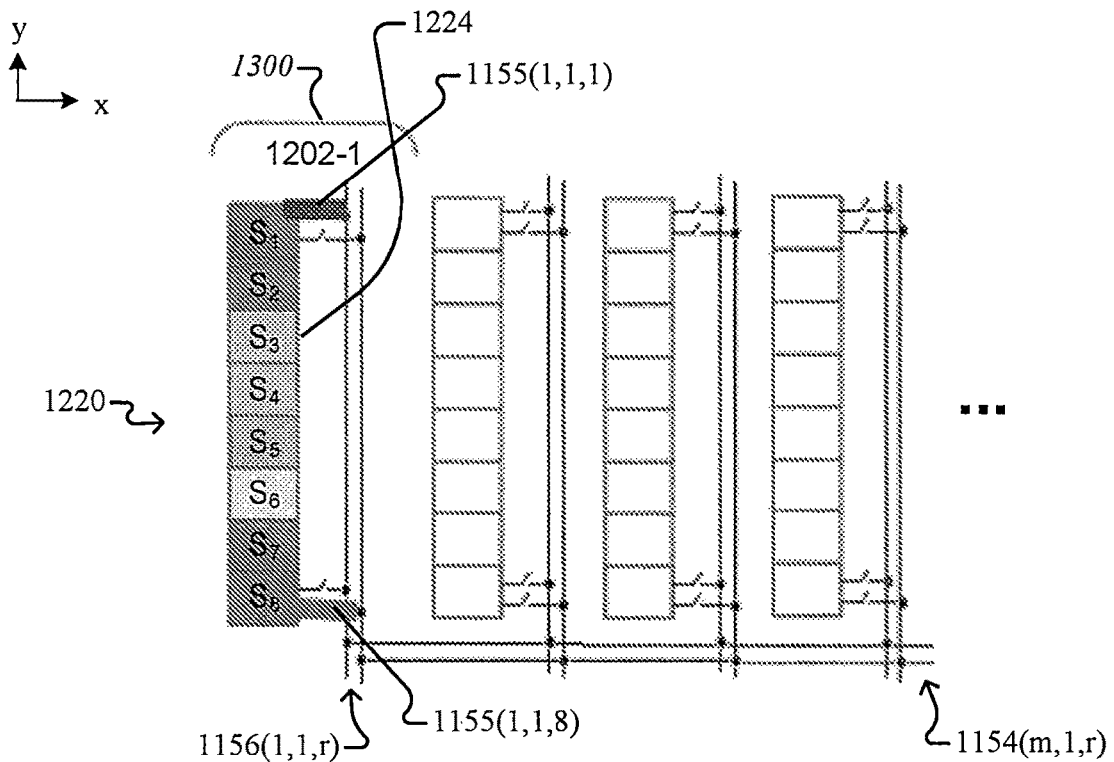
FIG. 13A
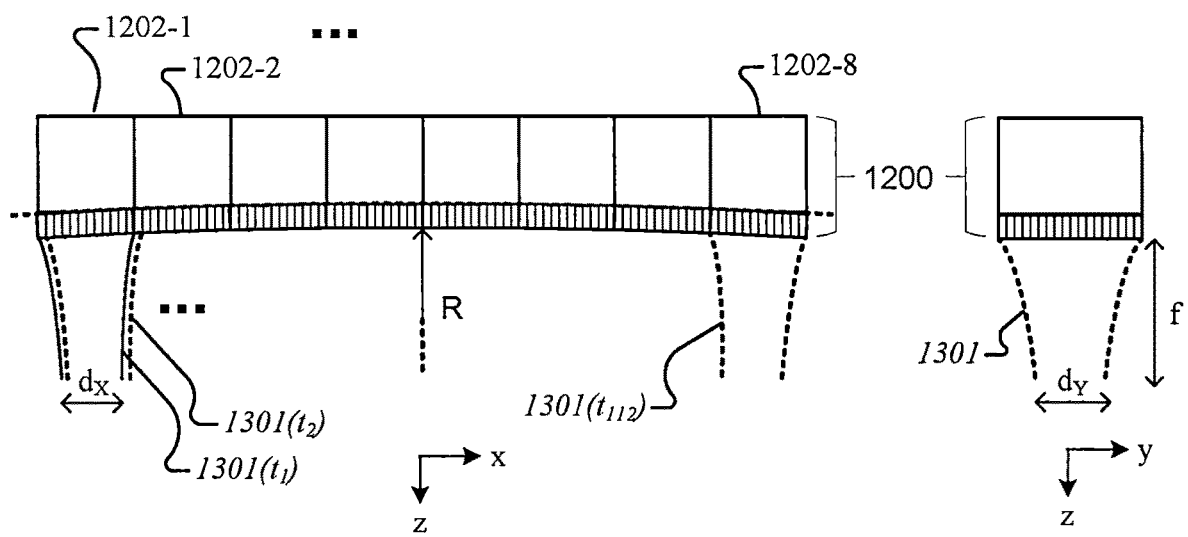
FIG. 13B
FIG. 13C

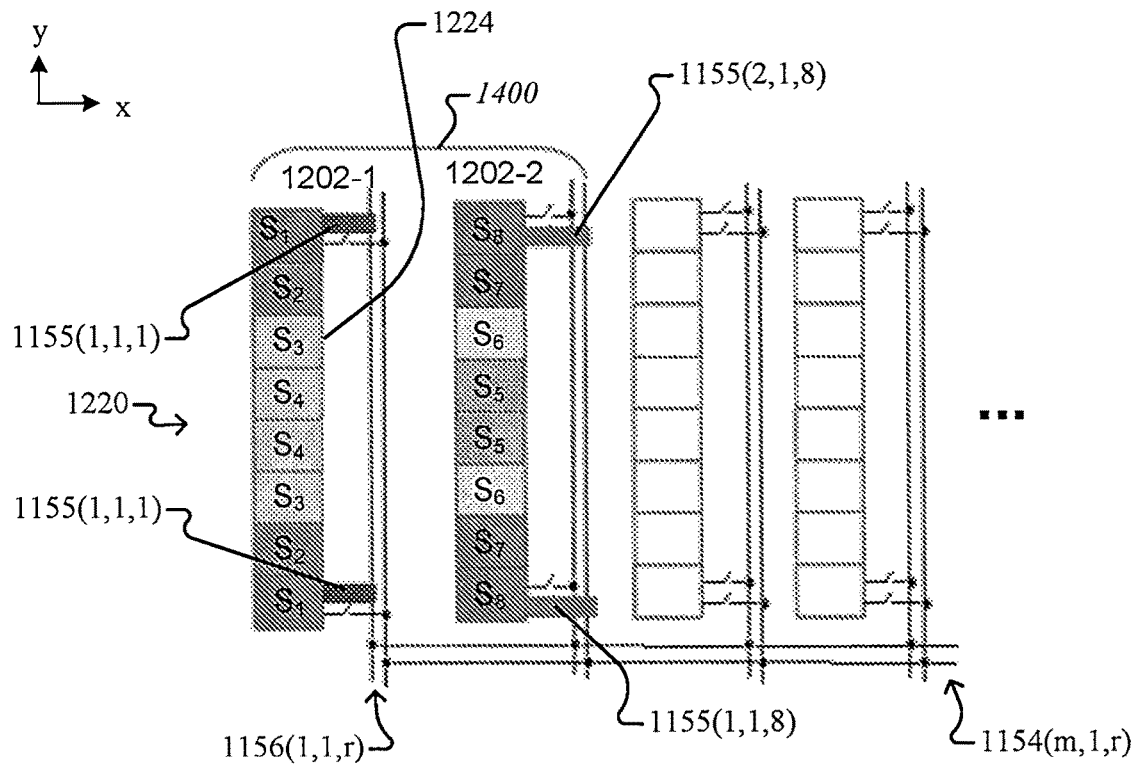
FIG. 14A
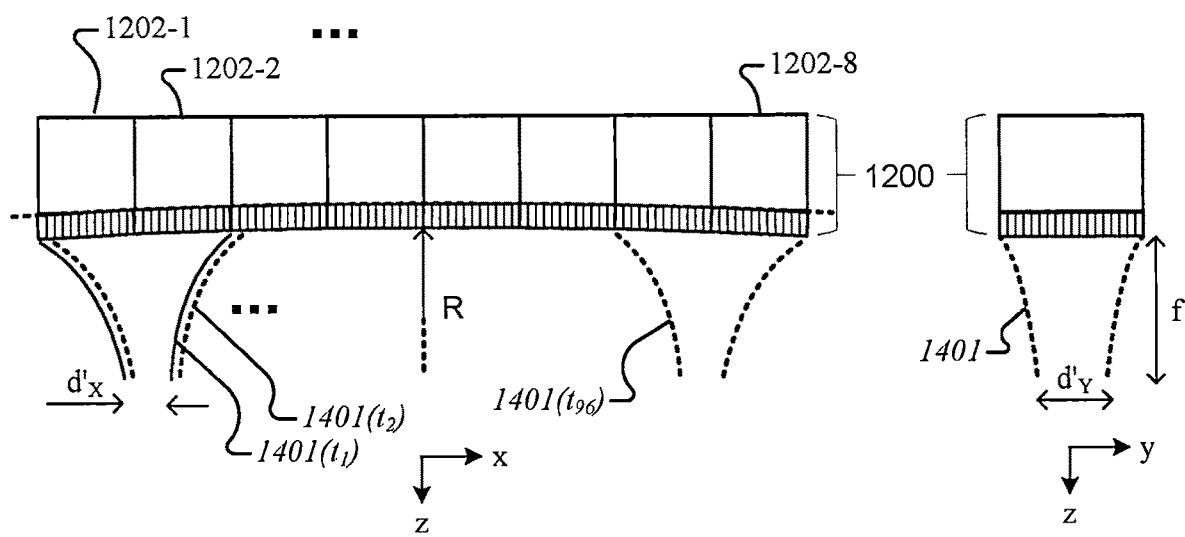
FIG. 14B
FIG. 14C

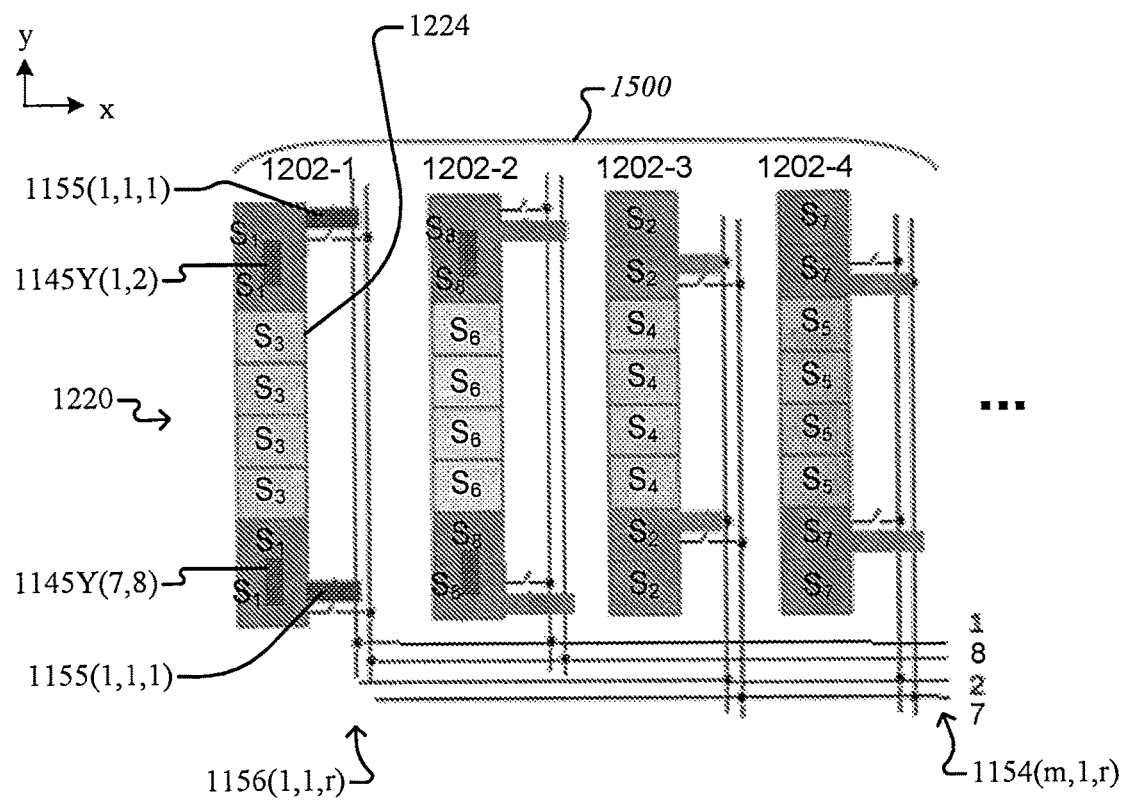
FIG. 15A
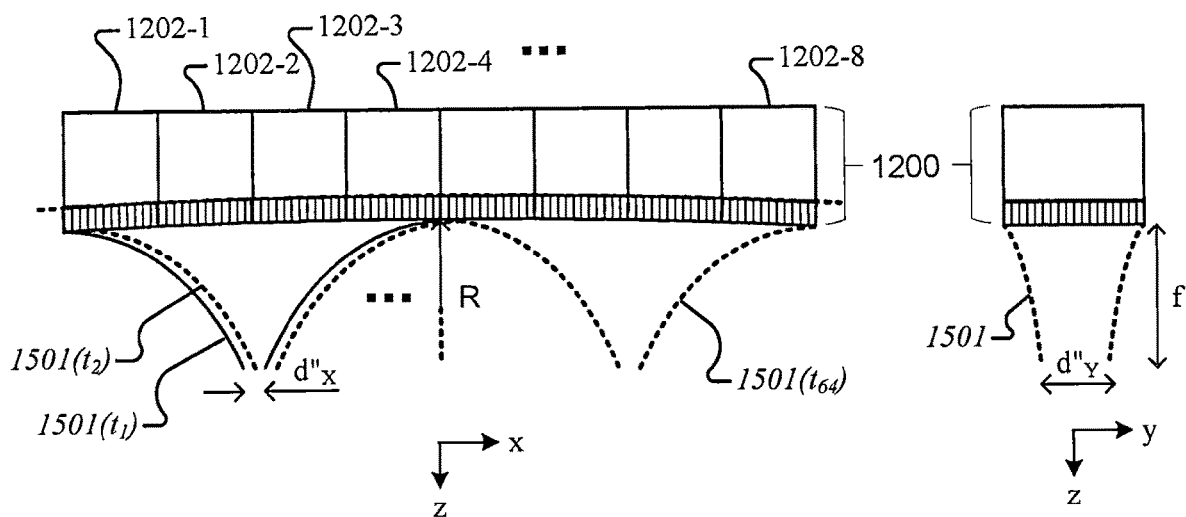
FIG. 15B
FIG. 15C

MODULAR PIEZOELECTRIC SENSOR ARRAY WITH CO-INTEGRATED ELECTRONICS AND BEAMFORMING CHANNELS

CROSS REFERENCE TO RELATED APPLICATIONS

This application is a National Stage Application under 35 U.S.C. § 371 and claims the benefit of International Application No. PCT/US2017/018537, filed Feb. 18, 2017 that claims priority to U.S. Provisional Application No. 62/297,008 filed Feb. 18, 2016. The disclosure of the foregoing applications are hereby incorporated by reference in their entirety.

STATEMENT AS TO FEDERALLY SPONSORED RESEARCH

This invention was made with government support under Contract No. P41-EB002182 awarded by the National Institutes of Health (NIH). The government has certain rights in the invention.

BACKGROUND

This specification relates to sensor arrays for imaging systems, such as for medical and non-destructive evaluation.

Large area two dimensional (2D) ultrasound arrays for imaging systems for medical and non-destructive evaluation (NDE/NDT) require a very large number of interconnections between the piezoelectric array and the respective buffering and switching electronics. This large number of interconnects presents a significant challenge for interconnection of the elements.

A number of different techniques have been proposed to address this issue. These include building the transducer arrays on a high density flexible circuit which is then connected to distal boards with switching and buffering electronics, laminating the transducer array directly to the electronic Application Specific Integrated Circuits (ASICs) with an intervening flex circuit or anisotropic conductive film (ACF), and building the transducers directly on top of the ASICs. Electrical attachment methods include high temperature methods such as bump-bonding solder attach and ACF bonding, as well as bonding that uses copper pillars or gold stud bumps. Additional more exotic methods include the use of novel micro-electro-mechanical system-based ultrasound transducers such as capacitive micro-machined ultrasonic transducers (cMUTs) and piezoelectric micro-machined ultrasonic transducers (pMUTs).

For optimal performance of an ultrasound transducer, it is preferable to utilize composites of piezo material and epoxy so that electromechanical coupling efficiency, $k_t$, can be increased. Further improvements can be realized by utilizing novel single crystal PMN-PT and PIN-PMN-PT materials which exhibit higher $k_t$ when compared to traditional PZT piezo materials. Both of these technologies lead to improved sensitivity and wider bandwidth, which can be critical to implementation of novel beamforming algorithms for improved imaging.

Furthermore, the large number of interconnects presents a significant challenge for beamforming. A number of different techniques have been proposed to address this issue, including sparse arrays, micro-beamformers (SAPs), and Reconfigurable Arrays.

SUMMARY

This specification relates to sensor arrays for imaging systems, such as for medical and non-destructive evaluation.

With regard to interconnection of the elements, issues with the previously proposed solutions are the following: systems utilizing flex circuits are significantly challenged by the limitation in trace and space widths in existing flex manufacturing technologies. These systems also incur significant parasitic capacitance due to the flex circuits between the transducers and the electronics. Improvements are obtained by laminating the transducers directly on top of the ASICs with intervening flex or ACF interconnect. However, these techniques require that the ASIC be thinned from 500 um to less than 50 um so it does not compromise the axial resolution of the probe by creating significant ringing in the transducer response. High temperature attachment methods are detrimental to the composites and single crystal materials which can become warped or de-poled. Monolithic methods which build the transducers directly on top of the ASICs such as cMUTs and pMUTS compromise the acoustic performance of the transducers themselves and require dedicated fabrication lines to improve yield.

The proposed invention creates a system with a co-integrated high sensitivity and wide bandwidth piezoelectric array and ASICs while mitigating the negative effects of previous implementations.

In one aspect, the disclosed technologies can be implemented as a modular array including one or more array modules. Each array module includes one or more transducer arrays, where each of the one or more transducer arrays includes a plurality of piezoelectric elements; a conducting interposer arranged and configured to provide acoustic absorbing backing for the one or more transducer arrays; and one or more Application Specific Integrated Circuits (ASICs). The conducting interposer and the one or more ASICs are in electrical contact with each other at a first direct electrical interface. Additionally, the conducting interposer and the one or more transducer arrays are in electrical contact with each other at a second direct electrical interface.

Implementations can include one or more of the following features. In some implementations, a width of the modular array along an azimuthal direction and a height of the modular array along an elevation direction can be roughly equal. In some implementations, a width of the modular array along an azimuthal direction can be greater than two times a height of the modular array along an elevation direction. In some implementations, a height of the conducting interposer is between 5λ and 20λ, and λ can be a wavelength of an ultrasound beam emitted by the modular array. In some implementations, a width of the modular array along an azimuthal direction can be greater than two times a height of the modular array along an elevation direction. In some implementations, pitches of the conducting interposer along azimuthal and elevation directions can match respective pitches of a transducer array.

In some implementations, the plurality of piezoelectric elements can include a composite of PMN-PT or PIN-PMN-PT piezoelectric material, and insulating filler material. For example, the insulating filler material can include a non-conducting epoxy, and the non-conducting epoxy can include one or more of a plasticizer, or scattering balloons. In some implementations, at least one of the one or more transducer arrays can include multiple acoustic matching layers.

In some implementations, the conducting interposer can include an electrically insulating grid frame with holes, and a conducting material that is acoustically attenuating and fills the holes of the electrically insulating grid frame. In some cases, a width along an elevation direction and a width along an azimuthal direction of the conducting material within a hole can each be at least 90% of respective pitches of a transducer array of the one or more transducer arrays. In some cases, the electrically insulating grid frame can include a non-conducting material that is configured to suppress transmission of lateral acoustic modes. Here, the non-conducting material can include one or more of a solid epoxy, an epoxy with a plasticizer, or an epoxy with scattering balloons. Further here, the conducting material can have a same acoustic impedance as the non-conducting filler material. In other cases, the conducting material can include scattering balloons. In other cases, the first direct electrical interface can include a silver loaded epoxy that is plated with a layer of nickel and a layer of gold. Also, the layer of nickel can be plated with a layer of palladium.

In some implementations, the first direct electrical interface can include a laminated layer of copper that is plated with a layer of nickel and a layer of gold. In some implementations, a surface of the conducting interposer adjacent the first direct electrical interface can include a crossing pattern of slots that are filled by silver loaded epoxy. In some implementations, the first direct electrical interface can include a conductive adhesive and either non-conductive spheres coated with a conducting metal or solid conductive spheres. In some implementations, the first direct electrical interface can include copper pillars, or gold stud bumps.

In some implementations, the modular array can include support structures that respectively support the at least two piezoelectric sensor modules; and a gimbal system mechanically coupled to the support structures and configured to cause, when actuated, changes in position and orientation of the at least two piezoelectric sensor modules relative to each other.

Another aspect of the disclosure can be implemented as a method for aligning the transducer arrays of the disclosed modular array. The method includes disposing a target in front of the one or more transducer arrays, where a distance from the target to each piezoelectric element of the one or more transducer arrays is approximately the same; measuring time of flight information corresponding to a distance between each respective piezoelectric element and the target by transmitting and receiving ultrasound from the respective piezoelectric element; storing the measured time of flight information at each element in memory; and calibrating measured signals at each respective piezoelectric element, while imaging with the modular array, by using the stored time of flight information.

Yet another aspect of the disclosure can be implemented as a method for manufacturing an array module. The method includes attaching an interposer to a semiconductor substrate of an Application Specific Integrated Circuit (ASIC) to form a sub-module; and attaching the sub-module to a transducer array using a low temperature method to form the array module.

Yet another aspect of the disclosure can be implemented as another method for manufacturing an array module. The method includes forming a block of electrically conducting, acoustically attenuating material on a surface of a transducer array; machining slots in the electrically conducting, acoustically attenuating material; filling the slots with an electrically insulating material to form a sub-module; coating the sub-module with a metal and patterning it to create pads; and attaching the sub-module pads to an Application Specific Integrated Circuit (ASIC) using a low temperature method to form the array module.

Yet another aspect of the disclosure can be implemented as an array module that includes a three dimensionally (3D) patterned interposer with two or more shelves; one or more transducer arrays in direct electrical contact with the 3D patterned interposer, where each of the one or more transducer arrays comprises a plurality of piezoelectric elements; and application specific integrated circuit (ASIC) chips assembled to the shelves of, and in direct electrical contact with, the 3D patterned interposer.

Implementations can include one or more of the following features. In some implementations, a surface of the 3D patterned interposer that is in direct electrical contact with the transducer arrays can be flat. In some implementations, a surface of the 3D patterned interposer that is in direct electrical contact with the one or more transducer arrays can be curved in one dimension. In some implementations, a surface of the 3D patterned interposer that is in direct electrical contact with the one or more transducer arrays can be curved in two dimensions. In some implementations, a surface of the 3D patterned interposer that is in direct electrical contact with at least one of the one or more transducer arrays can be shaped to conform to a curved transducer array.

In some implementations, the 3D patterned interposer can include multiple interposers which have been bonded together. In some implementations, the ASIC chips can be distributed parallel to an azimuthal direction of the array module. In some implementations, the ASIC chips can be distributed orthogonal to an azimuthal direction of the array module.

In some implementations, the 3D patterned interposer can include an embedded conducting path which connects a common top electrode of the one or more transducer arrays to respective terminals on the ASIC chips. In some implementations, the array module envelope can be covered by a conducting conformal coating that is connected to a common top electrode of the one or more transducer arrays as well as to a terminal on at least one of the ASIC chips.

With regard to beamforming, issues with the previously proposed solutions include compromise on the number of active elements or the absolute delay length as well as a reduction in the number of raw data channels available for sophisticated beamforming algorithms. Newly introduced programmable scanners offer 512-2048 system channels, with a broad range of imaging frequencies, arbitrary delays, apodization on all channels, large instantaneous dynamic range (e.g., 14 bits) and programmable transmit waveforms. There exists a need to integrate these highly versatile ultrasound processing systems with large 2D ultrasound arrays without compromising the available data for advanced beamforming algorithms.

The proposed invention creates an ultrasound system in which a large number of beamforming channels are mapped to a large number of sensor elements to realize a large area ultrasound array system. The system is composed of multiple modules where each comprises an ultrasound array directly coupled to respective processing ASICs and a support structure.

One way to address the issue of yield for a large array is to break the array up into smaller (e.g., 16×32 piezoelectric element) modules composed of individual sub-arrays assembled to their associated interface electronics. Each of the smaller modules can be screened and selected for yield from a larger pool of modules to form the final array and, thus, low cost and high yield methods can be developed for building large area arrays. The present application describes technologies for integrating one or more piezoelectric arrays in an array module that, in turn, can be integrated as part of a modular ultrasound (US) system. Thus, a system can be implemented with a co-integrated high sensitivity and wide bandwidth piezoelectric array and ASICs and/or an ultrasound imaging system in which a large number of beamforming channels are mapped to a large number of sensor elements to realize a large area ultrasound array system composed of multiple modules, where each module comprises an ultrasound array directly coupled to respective processing ASICs and a support structure.

As such, in another aspect, the disclosed technologies can be implemented as a modular ultrasound (US) system including at least two piezoelectric sensor modules, each including multiple piezoelectric elements arranged in groups of piezoelectric elements; and a multi-channel processing unit. A first element in a first of the groups in a first piezoelectric sensor module is coupled with a first interconnect bus line through a first interface unit, and a second element in the first group in the first piezoelectric sensor module is coupled with a second interconnect bus line through a second interface unit. A first element in a first of the groups in a second of the piezoelectric sensor modules is coupled with the first interconnect bus line through a third interface unit. The first interconnect bus line is further coupled to a first channel in the multi-channel processing unit, and the second interconnect bus line is further coupled to a second channel in the multi-channel processing unit. Additionally, the multi-channel processing unit is operable to transmit ultrasound pulses to the elements of the piezoelectric sensor modules in a first operating mode and receive sensor signals from the elements of the piezoelectric sensor modules in a second operating mode.

Implementations can include one or more of the following features. In some implementations, piezoelectric elements of each of the at least two piezoelectric sensor modules can be disposed as a rectangular array of piezoelectric elements with rows along an azimuthal direction and columns along an elevation direction. Here, the groups of piezoelectric elements are the columns of the rectangular array.

In some implementations, the interconnect bus lines are distributed along an elevation direction in the rectangular array. In some implementations, the interconnect bus lines can be distributed along an azimuthal direction in the rectangular array. In some implementations, the interconnect bus lines can be distributed along both azimuthal and elevation directions. Here, the modular ultrasound system can include switches arranged and configured to selectively connect channels in the multi-channel processing unit to horizontal interconnect bus lines in the first coupling mode, and vertical interconnect bus lines in the second coupling mode.

In some implementations, the interface units can include switching circuitry configured to selectively couple an element in a piezoelectric sensor module of the at least two piezoelectric sensor modules to another element in the first sensor module to form a paired grouping. In some cases, the switching circuitry can include a high voltage semiconductor switch. In some cases, the switching circuitry can include a low voltage semiconductor switch. In some cases, the switching circuitry can include an electronically-actuated micromechanical switch. In some cases, the switching circuitry can include a network of three switches which all share a first terminal, where one of the switches has its second terminal connected to ground. In some cases, the elements of the paired grouping can be physically located adjacent to each other in the piezoelectric sensor module. Here, the elements of the paired grouping can be part of a same one of the groups of piezoelectric elements. Alternatively, the elements of the paired grouping can be part of adjacent ones of the groups of piezoelectric elements. In some cases, the elements of the paired grouping can be symmetrically situated relative to an axis of the piezoelectric sensor module. In some cases, the elements of the paired grouping can be symmetrically situated relative to an axis of an active aperture of the piezoelectric sensor module.

In some cases, the switching circuitry are actuated by locally integrated control circuits. Here, the locally integrated control circuits can be configured to store one or more switch state bits internally. Further here, the locally integrated control circuits can be configured to switch between stored state bits one or more times during the second operating mode.

In some cases, the switching circuitry can be configured to form the paired grouping of the piezoelectric sensor module coupled with the first channel, and a paired grouping of another piezoelectric sensor module of the at least two piezoelectric sensor modules coupled with the second channel. In some cases, the switching circuitry can be configured to form (i) a first and second paired grouping of the piezoelectric sensor module coupled with a first channel, and (ii) a first and second paired grouping of another piezoelectric sensor module of the at least two piezoelectric sensor modules coupled to the second channel. In either of the foregoing two cases, the elements of the at least two piezoelectric sensor modules can be configured to respond to channels that operate at different frequencies.

In some cases, the switching circuitry can be configured to implement, in a first mode, a piezoelectric sensor module with an element pitch greater than half a transmit wavelength, and, in a second mode, a piezoelectric sensor module with the element pitch equal to or less than half of the transmit wavelength. In some cases, the switching circuitry can be configured to implement, in a first coupling mode, element grouping for a coarse sampling of the piezoelectric sensor module with a wide aperture, and, in a second coupling mode, another element grouping for a fine sampling of the piezoelectric sensor module with a narrow aperture.

In some implementations, the interface units can include electrical buffer circuits. Here, the electrical buffer circuits can be configured to be switched to an off state in which they draw minimal power. In some implementations, the first channel is configured to operate in a high power transmit mode while the second channel operates in a low power transmit imaging mode.

Details of one or more implementations of the disclosed technologies are set forth in the accompanying drawings and the description below. Other features, aspects, descriptions and potential advantages will become apparent from the description, the drawings and the claims.

BRIEF DESCRIPTION OF THE DRAWINGS

FIGS. 13A-13C show aspects of the disclosed modular ultrasound systems coupled with an US imaging system in accordance with an example of a coupling scheme.

FIGS. 14A-14C show aspects of the disclosed modular ultrasound systems coupled with an US imaging system in accordance with another example of a coupling scheme.

FIGS. 15A-15C show aspects of the disclosed modular ultrasound systems coupled with an US imaging system in accordance with yet another example of a coupling scheme.

DETAILED DESCRIPTION

Detailed examples of one or more implementations are included below. As will be appreciated, these are merely illustrative of the various possible implementations. While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Figure 1A:
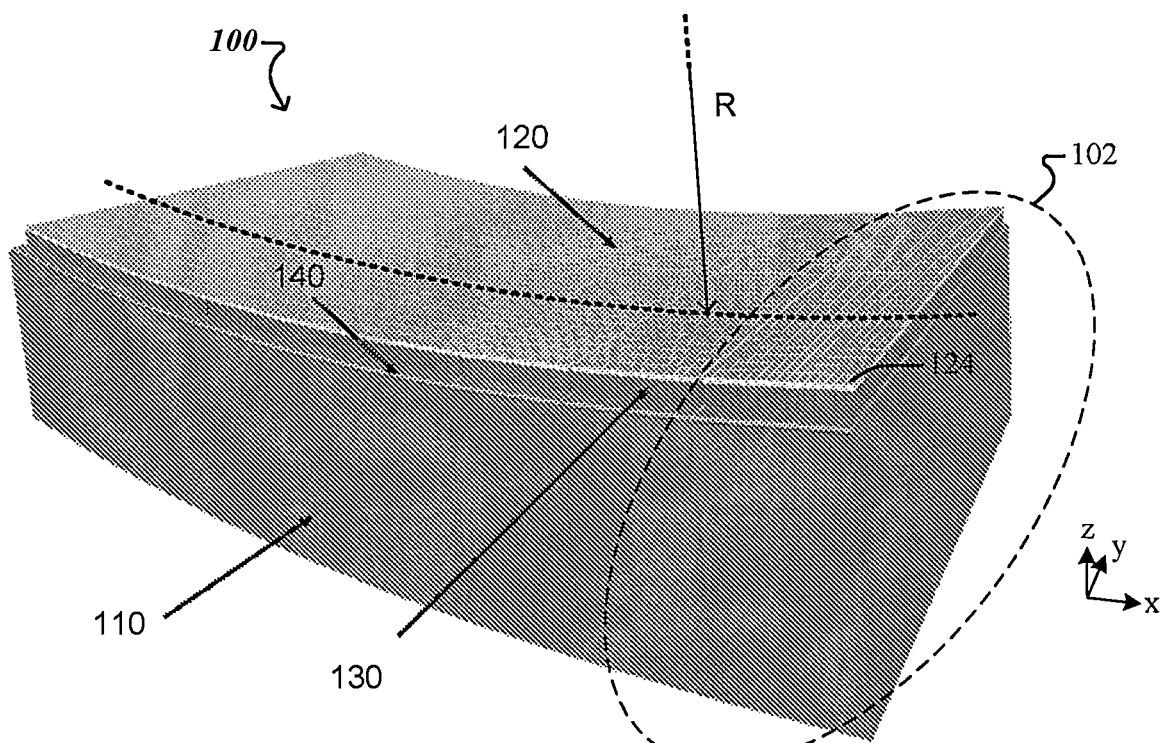
FIGS. 1A-1B and FIG. 2 show aspects of an example of a modular piezoelectric sensor array with co-integrated electronics.
Figure 1B:
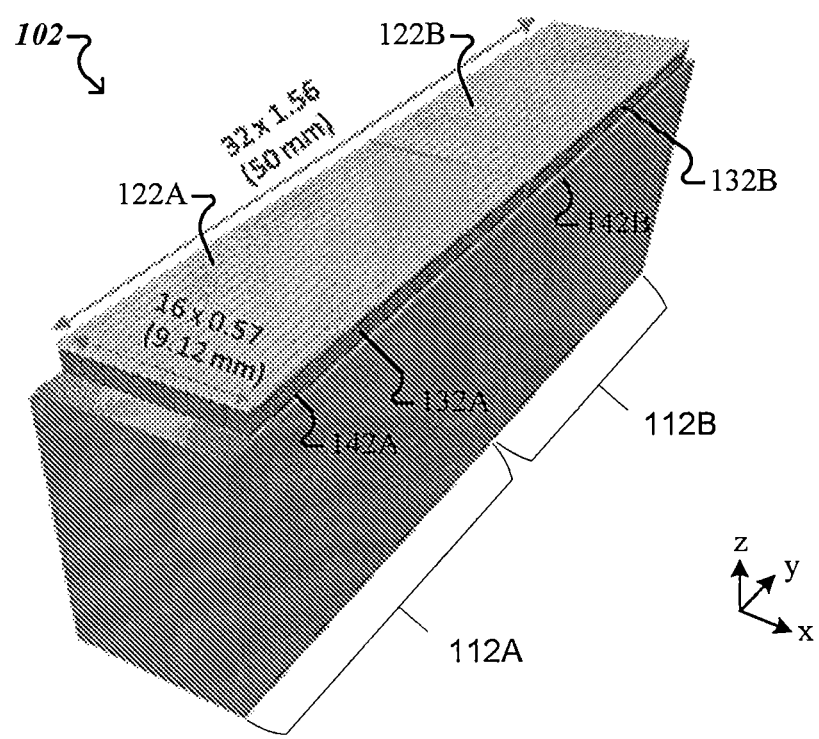

FIG. 1A shows an example of a modular transducer system 100 configured to implement the wider intended application of the proposed invention. The modular transducer system 100 includes a support structure 110, an array of ASICs 140 disposed on the support structure, and a large area array 120 of piezoelectric elements 124 that is directly electrically connected to the array of ASICs via an interconnecting interposer structure 130 (also referred to simply as an interposer). The modular transducer system 100 is constructed using multiple smaller transducer modules, for example like transducer module 102 shown in FIG. 1B. In this example, the transducer module 102 is composed of a pair of sub-modules each including a support structure 112A, 112B that houses an interface ASIC 142A, 142B, an interposer 132A, 132B and a transducer matrix 122A, 122B. As, in this example, each of the transducer matrices 122A, 122B has 16×16 piezoelectric elements, a transducer module 102 has 16×32 elements arranged in 32 rows extending along an elevation direction (e.g., along the y-axis) and 16 columns extending along an azimuthal direction (e.g., along the x-axis). In this manner, for a piezoelectric element 124 having a size of 1.6 mm in the elevation direction and a size of 0.6 mm in the azimuthal direction, the transducer module 102 has a total size of about 51.2 mm in the elevation direction and 9.6 mm in the azimuthal direction.

Referring again to FIG. 1A, a desired number of transducer modules 102 can be stacked along the azimuthal direction to form the modular transducer system 100. In some implementations, the array width (i.e., its size along the azimuthal direction) is 2, 5 or 10 times greater than the array height (i.e., its size along the elevation direction). In other implementations, the array width and the array height are the same, e.g., within 5%. Moreover, the transducer modules 102 of the modular transducer system 100 can be arranged and oriented relative to each other to cause a curvature of a surface of the large area array 120 of piezoelectric elements 124 to be zero, negative or positive corresponding to a piezoelectric element array that is respectively flat, concave or convex along the azimuthal direction. For the example of concave piezoelectric element array 120 from FIG. 1A, the modules are arranged with a radius of curvature that improves the focusing capability of the complete array for imaging of deep targets in tissue.

Figure 2:
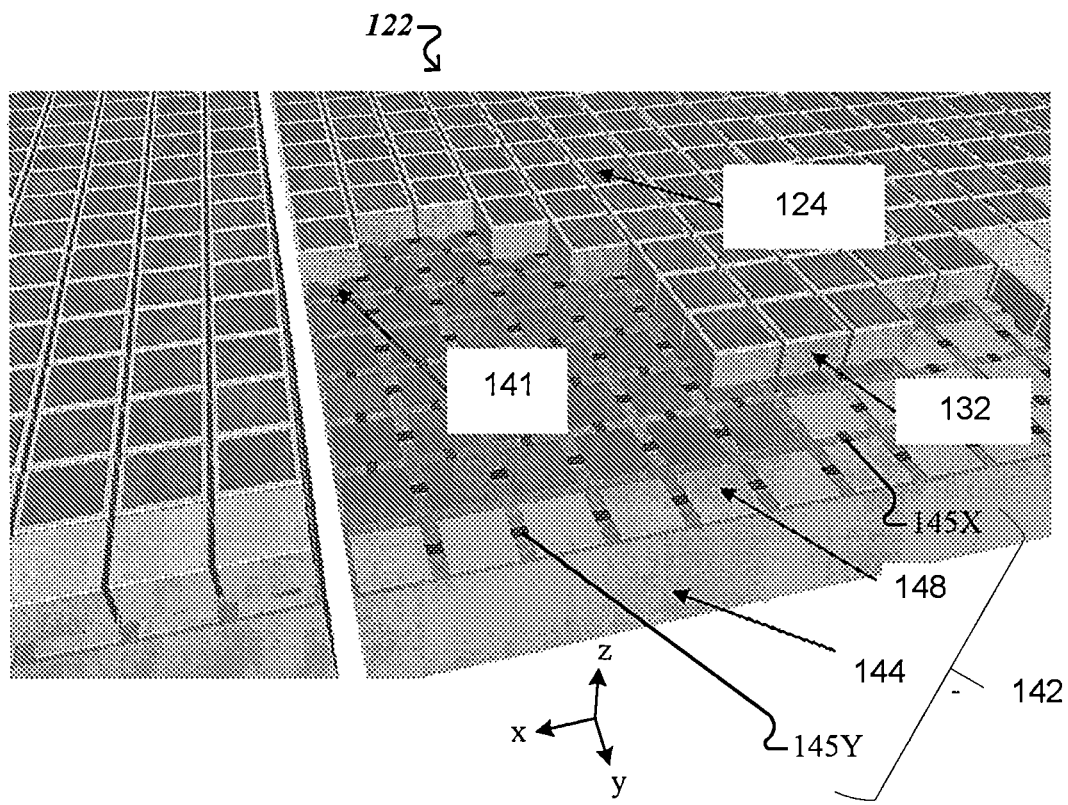

A more detailed cross-section of the transducer module 102 is shown in FIG. 2. Here, the connections from the ASIC 142 to the transducer matrix 122 are indicated by pads 148 on the ASIC substrate 144 which are then connected to the interposer 132 at a vertical attachment interface 141.

The ASICs 142 implement high voltage transmit functions as well as switching for multiplexing and pre-amplification of the receive signals. The ASICs can also incorporate analog to digital converters and/or digital or analog micro-beamforming functionality. In some implementations, adjacent piezoelectric elements 124 of the transducer matrix 122 can be selectively coupled together along the elevation direction using switches 145Y. Alternatively or additionally, adjacent piezoelectric elements 124 of the transducer matrix 122 can be selectively coupled together along the azimuthal direction using switches 145X.

The transducer matrix 122 can be composed of PZT material, PVDF, PMN-PT, PIN-PMN-PT or any other bulk material that is commonly used to fabricate transducer arrays. In some implementations, a composite of the piezoelectric material is used to form the piezoelectric elements 124 of the transducer matrix 122. This can either be a 2-2 composite that is used for linear arrays, or a 1-3 composite used for 2D arrays. The composite can be manufactured using a dicing saw and epoxy fill, or by micro-machining techniques. Additionally, a surface of the composite that faces a sample to be imaged can include one or more cast or laminated acoustic matching layers which help to improve the coupling of acoustic energy from the composite to a surface of the sample.

Figure 3:
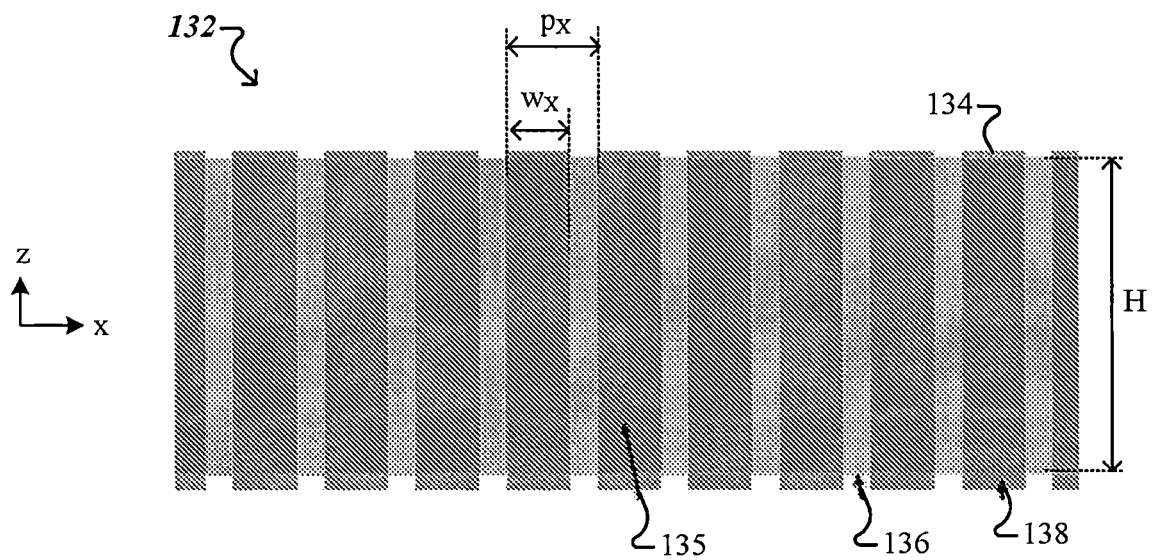
FIG. 3 shows an example of an interposer used to form direct electrical connections between a piezoelectric sensor array and its co-integrated electronics.

The interposer 132 provides backing for the transducer module 102, namely it absorbs US energy that propagates from the transducer matrix 122 backwards away from a surface to be imaged. Additionally, the interposer 132 transmits beam forming signals from the ASIC(s) 142 to the piezoelectric elements 124 and/or detected signals from the piezoelectric elements to the ASIC(s). FIG. 3 shows an example of such an interposer 132 that includes a substrate 136 formed from an insulating material with through holes that go from the top to the bottom of the substrate. The substrate 136, configured in this manner, is also referred to as an electrically insulating grid frame. The through holes of the substrate 136 are filled with a conductive material 135 to create thru-via interconnections from the top to the bottom of the substrate. These thru-via interconnections are also referred to as conducting pillars. In some implementations, the conducting material 135 (e.g., silver loaded epoxy) is also acoustically damping such that it serves as the backing material for transducer matrix 122. In some implementations, to further improve the acoustic absorption of the conducting material 135, it can be filled with embedded glass or phenolic micro-balloons.

A pitch $p_X$ along the azimuthal direction (or a pitch $p_Y$ along the elevation direction) of the through holes of the substrate 136 corresponds to an azimuthal pitch (or elevation pitch) of the transducer matrix 132. In some implementations when the transducer matrix 122 is implemented as a linear array, the azimuthal pitch or the elevation pitch or both are of order $\lambda$, where $\lambda$ is the wavelength of the US wave emitted/received by the transducer matrix. In some implementations when the transducer matrix 122 is implemented as a phased array, the azimuthal pitch or the elevation pitch or both are of order $\lambda/2$. Additionally, the transducer matrix 122 can be operated using multiple frequencies, and the azimuthal pitch can be different from the elevation pitch. As such, an example of transducer matrix 122 can be operated at 1.25 MHz, 2.5 MHz, and 5 MHz. In this example, if the transducer matrix 122 is assumed to be a linear array in azimuth, then the azimuthal pitch is designed to be $\lambda$ at 5 MHz. In this manner, the azimuthal pitch can be $0.25\lambda$ at 1.25 MHz (with the elements grouped as described below in connection with FIGS. 15A-15C). If the transducer matrix 122 is assumed to be a phased array for those frequencies, then a 5 MHz operating mode can use an azimuthal pitch of $0.5\lambda$, and a 1.25 MHz operating mode can use an azimuthal pitch of $0.125\lambda$. In elevation, a coarser pitch (e.g. $1.5\lambda$, $2\lambda$, $2.5\lambda$) can be used, especially if the US beam emitted by the transducer matrix 122 is not being steered in elevation (e.g., for an application that is not suitable for volumetric imaging because the US beam is only being focused in elevation).

Further, a width $w_X$ along the azimuthal direction (or a width $w_Y$ along the elevation direction) of each column of conducting material 135 is a fraction of the corresponding pitch $p_X$ (or pitch $p_Y$), for instance $w_X$ (or $w_Y$)=10%, 30%, 50%, 90%, or 95% of $p_X$ (or $p_Y$). For large percentages, the conducting material 135 absorbs most of the back-emitted US energy, whereas for small percentages the insulating material 136 absorbs most of the back-emitted US energy. If the insulating material 136 and the conducting material 135 were designed to cause similar attenuation and/or have similar acoustic impedance, then intermediate percentages can also be used.

Moreover, a height H of each column of conducting material 135 is selected such that a desired degree of attenuation is caused by the interposer backing. For instance, the height H can be 5, 10 or $20\lambda$. For instance, preferably H$\approx 10\lambda$, depending on the attenuating properties of the combination of conducting material 135 and insulating material 136. For instance, H$\approx 5\lambda$ is possible when the material combination has very good attenuating properties, but H$\approx 20\lambda$ may be necessary for a weakly attenuating material.

The substrate 136 can be fabricated using standard interposer materials including FR4 material, ceramic, glass, or silicon. However, in some embodiments, the substrate 136 consists of a frame fabricated by laser or lithographic micro-machining of a starting slab of material (e.g. laminated polyimide film, polyether ether ketone, or acrylic). The substrate 136 creates a frame which can then be filled with the conductive backing material 135 and cured. The top and bottom of the substrate 136 can be coated with patterned gold pads 134 and 138, respectively, which provide an ohmic connection to the transducers 124 and to the ASICs 142. The substrate 136 can also be optimally fabricated using rapid-prototyping fabrication techniques such as stereo-lithography or microinjection molding. Multiple different materials can be used to perform such rapid-prototyping fabrication techniques including (but not limited to) cured epoxy resin, and epoxy resin with embedded scatterers.

In some implementations, the interposer substrate frame is first created, using a 3D printer, as a sacrificial layer that forms an insulating frame. This insulating frame is then filled with conducting backing material 135 which is cured. After curing of the conducting backing material 135, the 3D printed sacrificial material is removed creating freestanding backing pillars. The space between the pillars can be filled with an epoxy resin 136 for structural stability. The epoxy resin 136 can be modified using a plasticizer and/or embedded glass or phenolic micro-balloons to reduce propagation of lateral modes.

The interposer 132 can be further fabricated by casting a uniform block of electrically conducting, acoustically attenuating material on the surface of the composite transducer array 122, dicing or micro-machining slots in the block to create the conducting backing 135, filling the slots with an electrically isolating material 136 (e.g. epoxy), and then coating the back of the interposer 132 with a metal film by sputtering or other semiconductor fabrication techniques. The metal film can then be patterned by dicing or using semiconductor lithography to create the pads 134, 138 for connection to the ASIC 142. This latter method can provide excellent acoustic connection of the acoustic backing to the transducer array 122 for optimal performance.

Interconnection of the interposer 132 to the transducers 124 and to the ASICs 142 can be accomplished using known assembly techniques which have been developed by the electronics industry. These include solder attach, gold stud bumps, indium bumping, and thermo-compression bonding. In addition, metal-coated micro-spheres can be attached between the ASIC pads 148 and the interposer pads 138. However, in some embodiments, a low temperature conducting adhesive is used to attach the interposer 132 to the ASICs 142 and to the transducer matrix 122 above it. An underfill material (e.g., epoxy) can be used between the ASIC 142 and the interposer 132 and between the interposer and the transducer matrix 122 to improve the reliability of the assembly. In the latter cases, the underfill material can also ensure an acoustically matched interface between the transducer matrix 122 and the interposer 132.

Moreover, the bottom surface of the interposer 132 can be adapted to improve assembly to the ASIC(s) 142 in the following ways. In some implementations, a layer of silver loaded epoxy can be cured on the bottom surface of the interposer 132. Here, in some cases, the bottom surface of the interposer 132 can have a crossing pattern of slots that are filled by the silver loaded epoxy. The cured silver loaded epoxy is then plated with a layer of nickel and a thin layer of gold. In some cases, the layer of nickel can be plated with a layer of palladium. In other implementations, a layer of copper can be laminated on the bottom surface of the interposer 132. The laminated layer of copper is then plated with a layer of nickel and a thin layer of gold.

Figure 4:
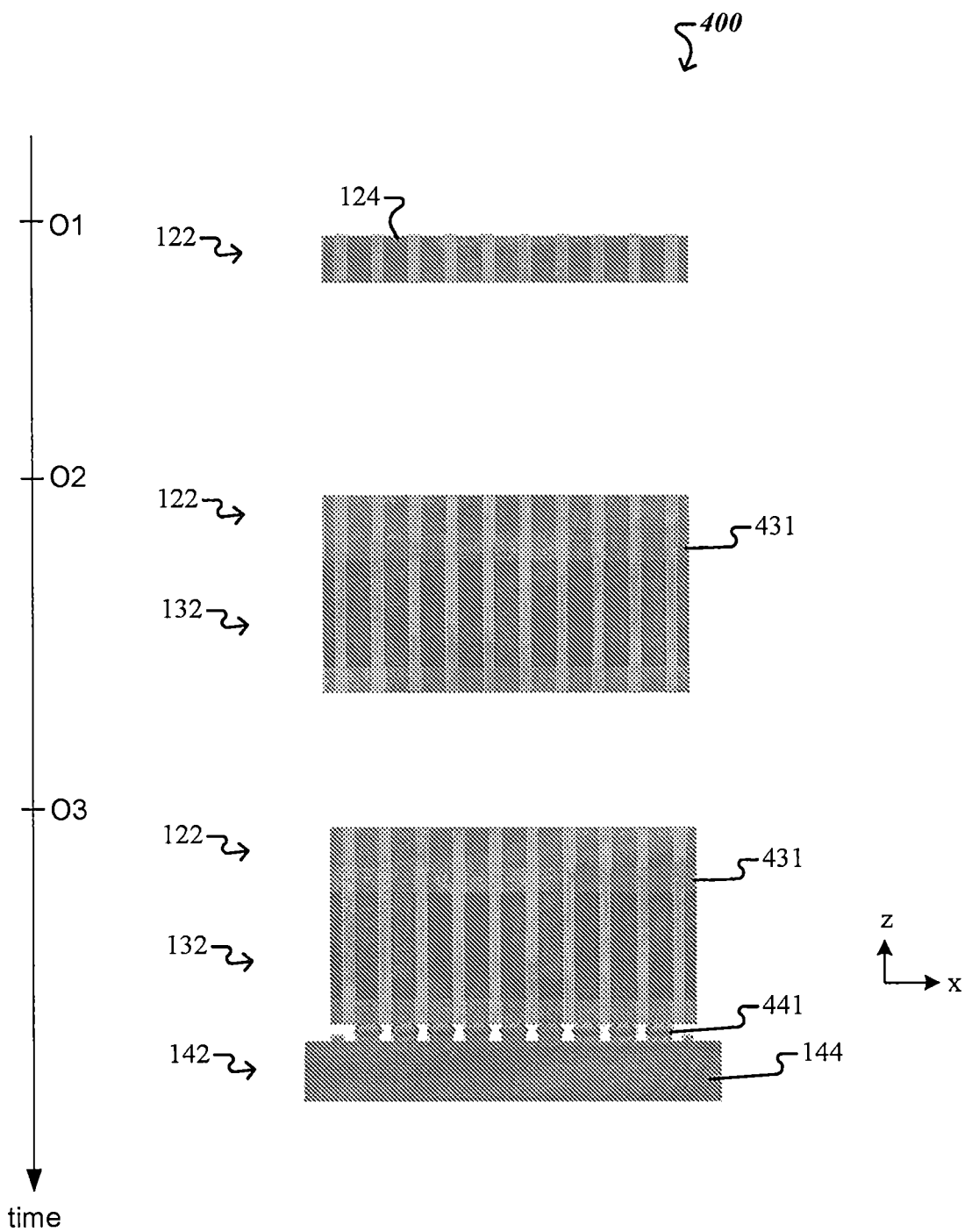
FIGS. 4-7 show examples of processes for attaching an interposer between a piezoelectric sensor array and its co-integrated electronics.

FIG. 4 illustrates one example of a method 400 for assembly of the transducer matrix 122 to the interposer 132 and the ASIC 142's substrate. At O1, the transducer matrix 122 is received preferably as a 1-3 composite of PMN-PT or PIN-PMN-PT material that has an array of conducting electrode metal pads on the bottom. At O2, the transducer matrix 122 is bonded to the interposer 132 using one of the techniques described above. In this manner, a transducer bonding interface 431 is formed between the transducer matrix 122 and the interposer 132. At O3, the interposer and transducer matrix assembly is attached to the ASICs 142 directly to form an ASIC bonding interface 441 between the interposer 132 and the substrate 144 of the ASIC. The ASIC's substrate 144 can have an array of pads (e.g., 148 shown in FIG. 2) which have been bumped with low temperature conducting adhesive beforehand. At O4 (not shown in FIG. 4), the completed assembly is then cured in an oven at low temperature. An alternate method to that shown in FIG. 4 is to first form the ASIC bonding interface 441 to assemble the interposer 132 to the ASICs 142, and then form the transducer bonding interface 431 to assemble the transducer matrix 122 to the interposer and ASIC assembly. This latter method is advantageous since a high temperature attachment process can be used to form the ASIC bonding interface 441 between the interposer and the ASICs while a low temperature attachment process can be used for forming the transducer bonding interface 431 thereby preventing damage of this temperature-sensitive part of the assembly.

Figure 5:
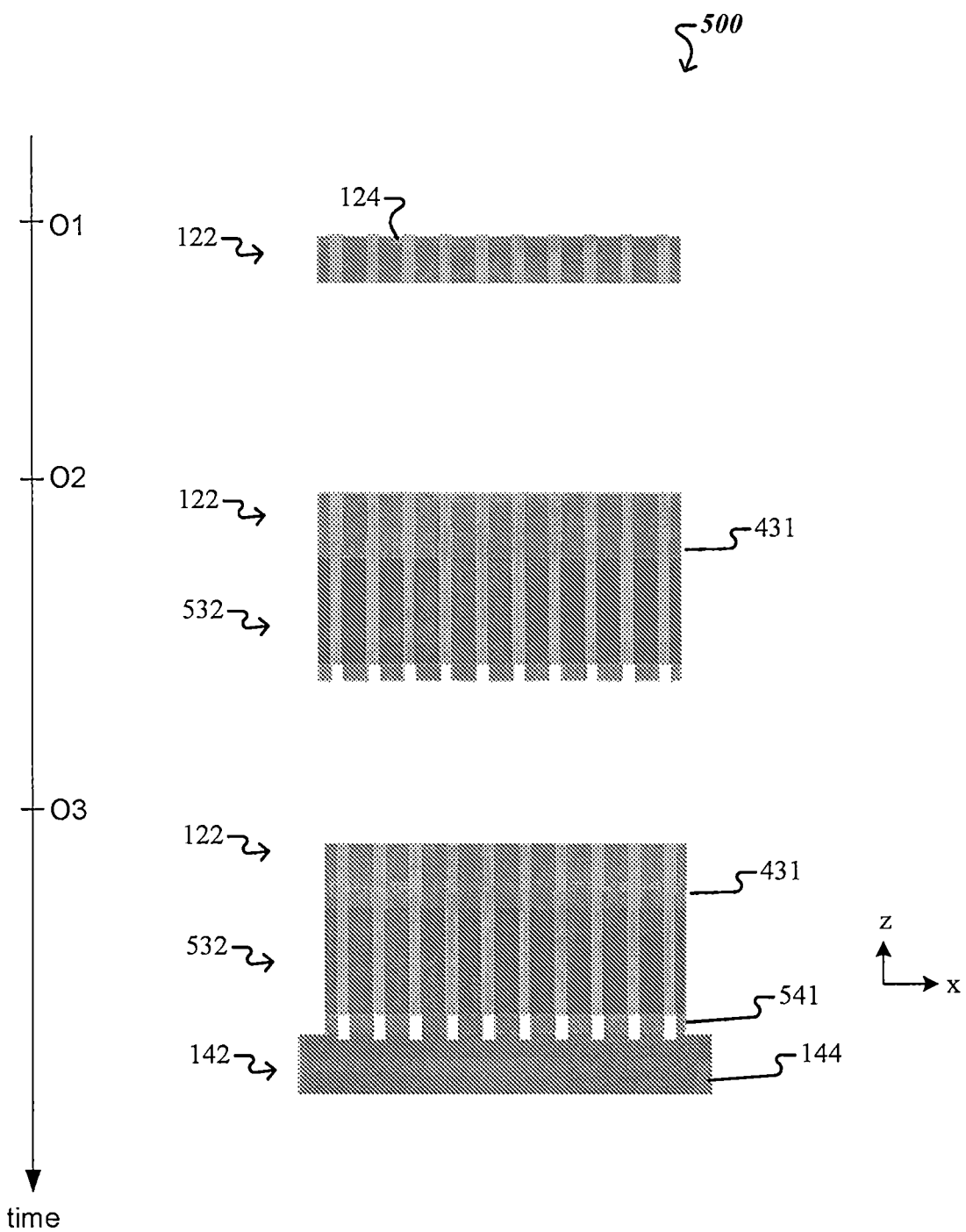

FIG. 5 shows another example of an assembly method 500. Operations O1 and O2 of the method 500 can be similar to the corresponding operations of method 400. Except the interposer 532 itself is received with conducting bumps which are created by sub-dicing the electrically insulating grid frame 136 to expose the central conducting material 135. At O3, the interposer and transducer matrix assembly is attached to the ASIC 142 directly to form an ASIC bonding interface 541 between the interposer 532 and the substrate 144 of the ASIC. In this case, the ASIC interface pads will have been prepared ahead of time with an inert metallization capable of forming an ohmic contact with the interposer. Non-conducting underfill material is used to secure the mating components to each other.

Figure 6:
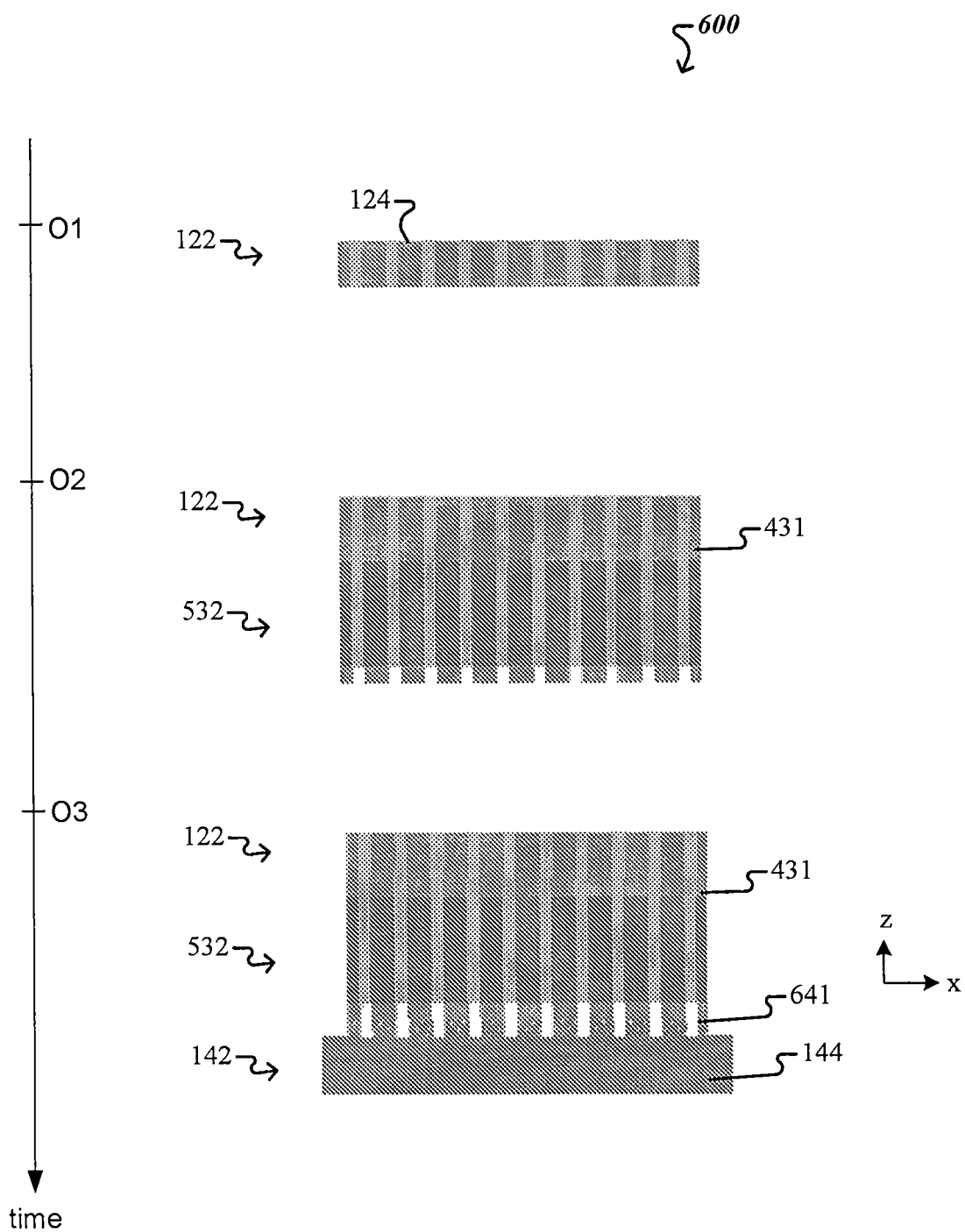

FIG. 6 shows yet another example of an assembly method 600. Operations O1 and O2 of the method 600 can be similar to the corresponding operations of method 500. Moreover, at O3, conductive epoxy is used to form an ASIC bonding interface 641 between the interposer 532 and the substrate 144 of the ASIC 142 for the attachment of the ASIC to the interposer and composite assembly. In some cases, it may be beneficial to sub-dice the front side of the transducer matrix 122 after bonding to the interposer 532, e.g., between operations O1 and O2, such as the case where the bonding interface 431 consists of a uniform conducting epoxy layer.

Figure 7:
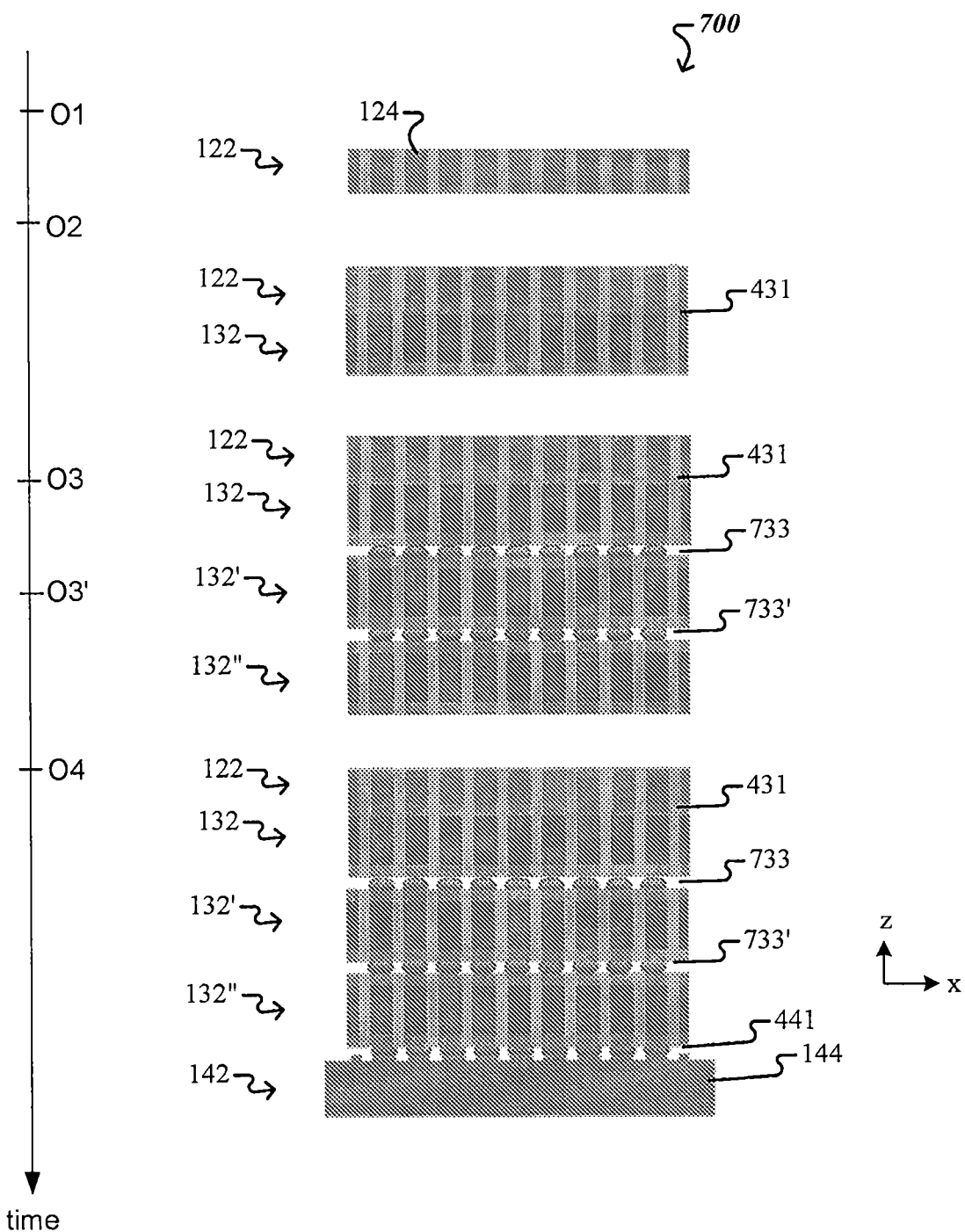

For some fabrication methods, the interposer 132 may be limited in the height which can be obtained. The height of the interposer 132 is important for properly attenuating the coupled acoustic energy from the transducer matrix 122. In this situation, multiple thinner interposers 132, 132', 132" can be stacked as shown in FIG. 7 to realize the correct attenuation distance for the backing. FIG. 7 shows an example of a method 700 for assembling transducer matrix 122 to an ASIC 142 through a multi-layer interposer formed from interposers 132, 132', 132". Here, operations O1, O2 and O4 of method 700 can be similar to the corresponding operations O1, O2 and O3 of method 400. For method 700, at O3, a first inner bonding interface 733 is formed using an electrically isolating and acoustically transparent material (e.g., epoxy) to fill the space between the interposers 132 and 132' that is in-between their conducting connections 135 in order to insure good coupling of the multiple layers of the backing stack. At O3', a second inner bonding interface 733' is formed in a similar manner to the one used at O3. Conducting backing material 135 for interposers 132, 132', 132" may be different, thereby enabling a graded attenuation profile.

Figure 8:
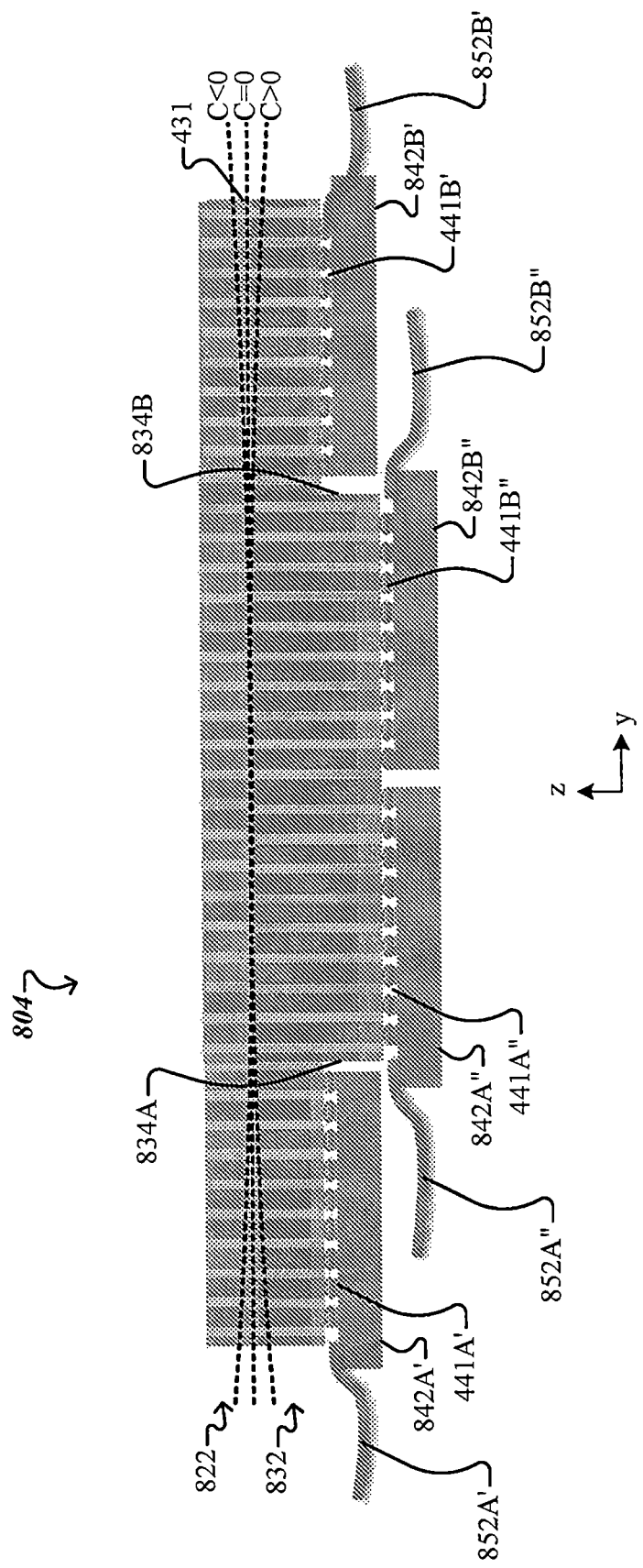
FIG. 8 shows an assembly of a piezoelectric sensor array co-integrated with electronics via an interposer having multiple shelves.

FIG. 8 shows an assembly 804 that includes a large array 822 of piezoelectric elements (also referred to as a transducer matrix) that extends along the elevation direction (along the y-axis), a 3D-machined interposer 832, and multiple ASICs 842A', 842A", 842B', 842B" with their associated flex circuits 852A', 852A", 852B', 852B". The interposer 832 in this case can be manufactured by laser milling or micro-machining methods such that it contains multiple shelves (e.g., two shelves) for housing the multiple ASICs, adjacent shelves separated by respective shoulders 834A, 834B. The importance of this embodiment is that large ASICs cannot be fabricated with high yield and multiple smaller ASICs provide much greater chance of yielding a complete working assembly 804. In addition, attaching multiple ASICs to a flat interposer creates a challenge for bringing out the ASIC interconnects to an imaging system. This challenge can be addressed using high voltage through-Si vias, however the technology is expensive and not mature enough for building a large inexpensive array. For a small number of signal channels, this challenge could also be addressed by laminating a continuous flex circuit between the entire length of the interposer and the associated ASICs. This later solution may limit the number of uniquely assigned signal channels which can be brought into the array due to the coarse pitch available for flex circuit fabrication. Note that an attach method similar to method 400 can be used to form the transducer bonding interface 431 between the array 822 of piezoelectric elements and the interposer 832, and the ASIC bonding interfaces 441A', 441A", 44B', 441B" between the interposer and the respective ASICs 842A', 842A", 842B', 842B".

Moreover, the transducer bonding interface 431 can be shaped (e.g., either by controlling its thickness along the elevation direction or by appropriately shaping the interposer 832) such that the array 822 of piezoelectric elements has a zero, negative or positive curvature, C, along the elevation direction. In this manner, the assembly 804 can be used as part of the transducer module 102 shown in FIG. 1B to impart a desired curvature along the elevation direction to the transducer module.

Figure 9:
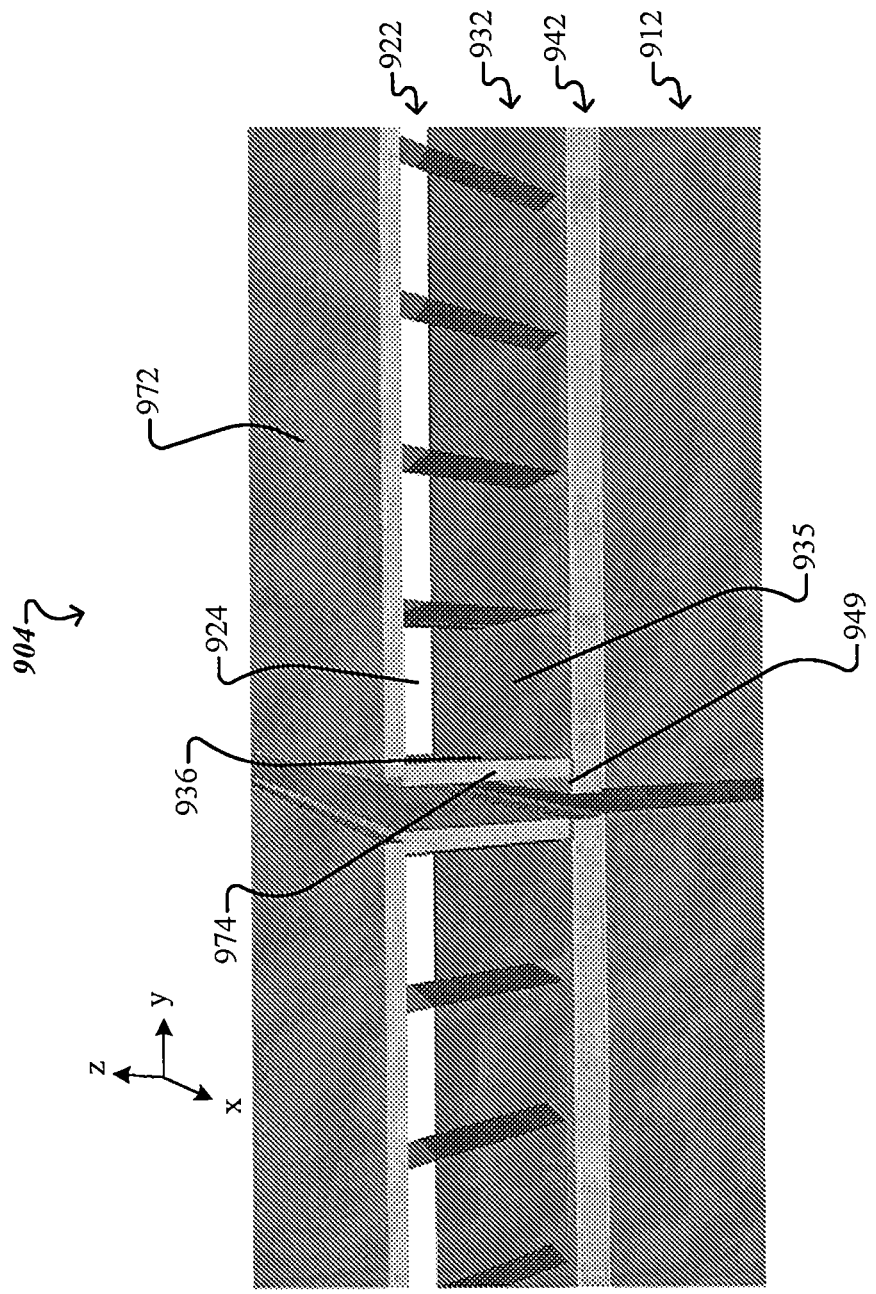
FIG. 9 shows examples of ground connections of piezoelectric elements of a piezoelectric sensor array.

The transducer matrix 822 or 122 further includes a front side electrode that provides a common ground connection shared by all elements of the transducer matrix. FIG. 9 illustrates how the front side electrode 972 providing the common ground connection is electrically coupled to an ASIC associated with the transducer matrix. In this example, an assembly 904 includes a transducer matrix 922 coupled, via an interposer 932, with ASICs 942 disposed on a support structure 912. Here, the interposer 932 includes conducting backing 935 filling an insulating frame 936 (e.g., formed from epoxy using methods described above). The front side electrode 972 can be formed, e.g., by sputtering Cr/Au on a top surface of the piezoelectric elements 924 of the transducer matrix 922. In this manner, the front side electrode 972 provides a common ground shared by all the piezoelectric elements 924 of the transducer matrix 922 and, thus, it allows for the piezoelectric elements to be directly connected to a ground on the ASIC 942. The connection of the front side electrode 972 with the ground on the ASIC 942 is formed using a ground plug 974 of the interposer 932. Note that during operation of the transducer matrix 922, the ground of the ASIC 942 is tied to the ground of an US imaging system.

The ground plug 974 shown in FIG. 9 can be formed by first dicing a respective slot in the fabricated interposer 932 and transducer matrix 922, and then casting a plug of Ag-filed epoxy. The latter is located such that it contacts both the front side electrode 972 and a ground ring 949 of the ASIC 942. In other implementations, the ground plug 974 can be replaced with another conducting path that is formed between the front side electrode 972 and the ASIC 942's ground by spraying a conducting conformal coating over the envelope of the assembly 904. This latter method would yield a thin ground connection which is advantageous for reducing the acoustic dead area which surrounds each module.

Figure 10B:
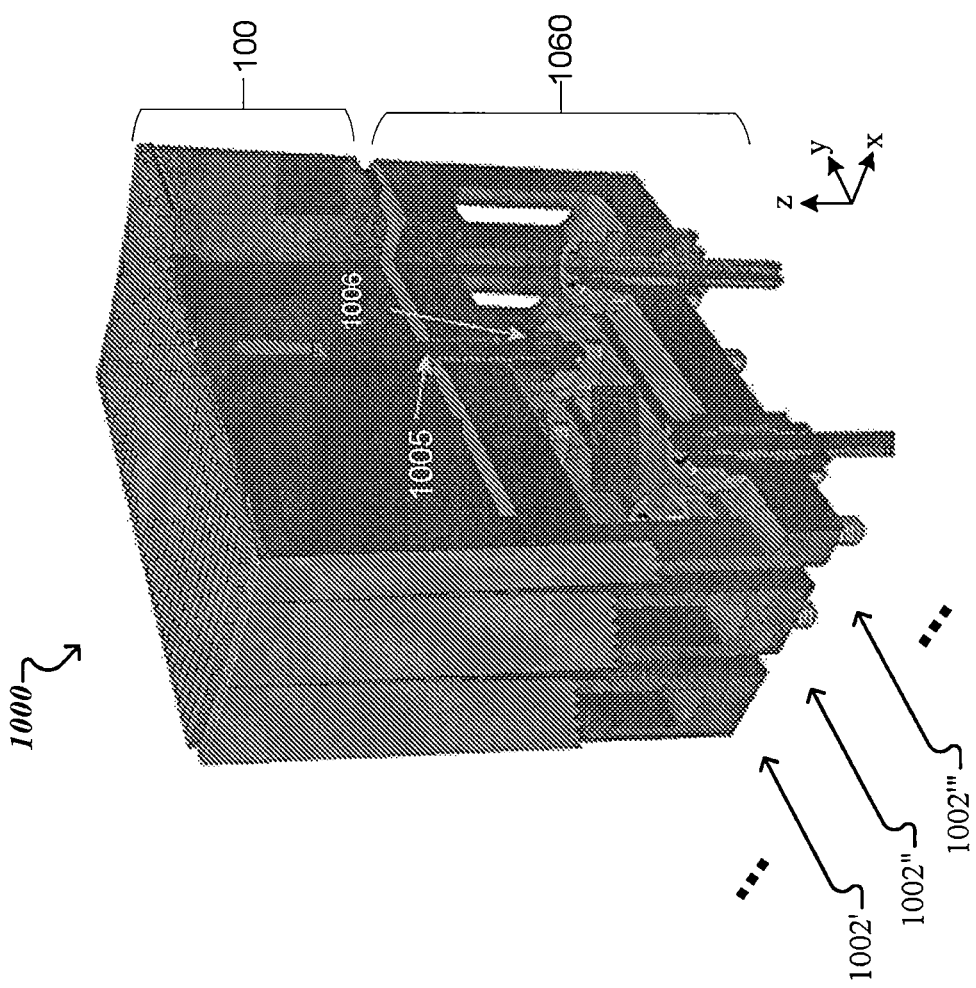
FIGS. 10A-10B show aspects of a modular piezoelectric sensor array with co-integrated electronics coupled with an example of a gimbal-based alignment system.
Figure 10A:
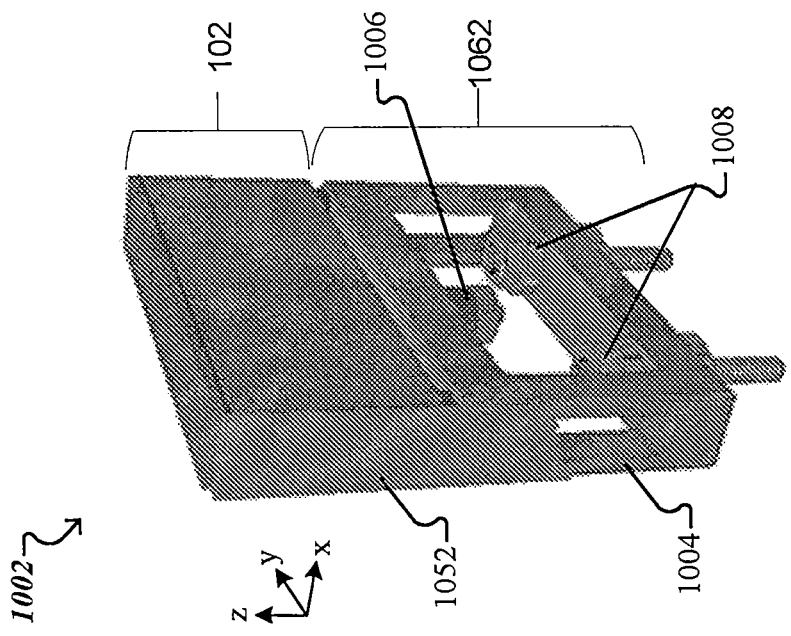

FIG. 10A shows an example of a transducer module assembly 1002 that includes a transducer module 102 (as described above in connection with FIG. 1B), a chassis module 1062 to support the transducer module, and a flex circuit module 1052 to couple the transducer module to a US imaging system. In some implementations, the chassis module 1062 can include a frame 1004 (e.g., made from anodized aluminum), a gimbal 1006 for adjusting a position of the transducer module 102 relative to the frame, and bulkhead mounting hardware 1008 for mounting the transducer module 102 to a desired US imaging system. FIG. 10B shows a portion of an example of a transducer system 1000 composed of a tiling of N×1 of the module assemblies 1002, e.g., 1002', 1002", 1002"', etc. In this manner, the modular transducer system 100, described above in connection with FIGS. 1A-1B, can be integrated in the transducer system 1000 together with a chassis 1060, formed from chassis modules 1062 described above in connection with FIG. 10A. The system of gimbals 1006 can be used to adjust, over 6 degrees of freedom around corresponding pivot points 1005, a position and orientation of adjacent transducer modules 102 of the modular transducer system 100 to minimize size of gaps between edges, and slope difference between surfaces, of their respective transducer matrices 122. In another embodiment, the gimbal could be an electro-actively controlled structure (e.g. a MEMs or piezoelectric device) enabling remote and incremental adjustment for fine tuning the alignment during use.

In some implementations, the plurality of transducer arrays of the transducer system 1000 can be aligned using the following example of an alignment method. A target is disposed in front of the plurality of transducer arrays of the transducer system 1000, such that a distance from the target to each piezoelectric element of the one or more transducer arrays is the same. Time of flight information corresponding to a distance between each respective piezoelectric element of the plurality of transducer arrays and the target can be measured by transmitting and receiving ultrasound from the respective piezoelectric element. The measured time of flight information at each element is stored in memory. Moreover, signals measured at each respective element are calibrated during use of the transducer system 1000 for standard imaging (i.e., imaging performed outside of the foregoing alignment method) by using the stored time of flight information.

Figure 11:
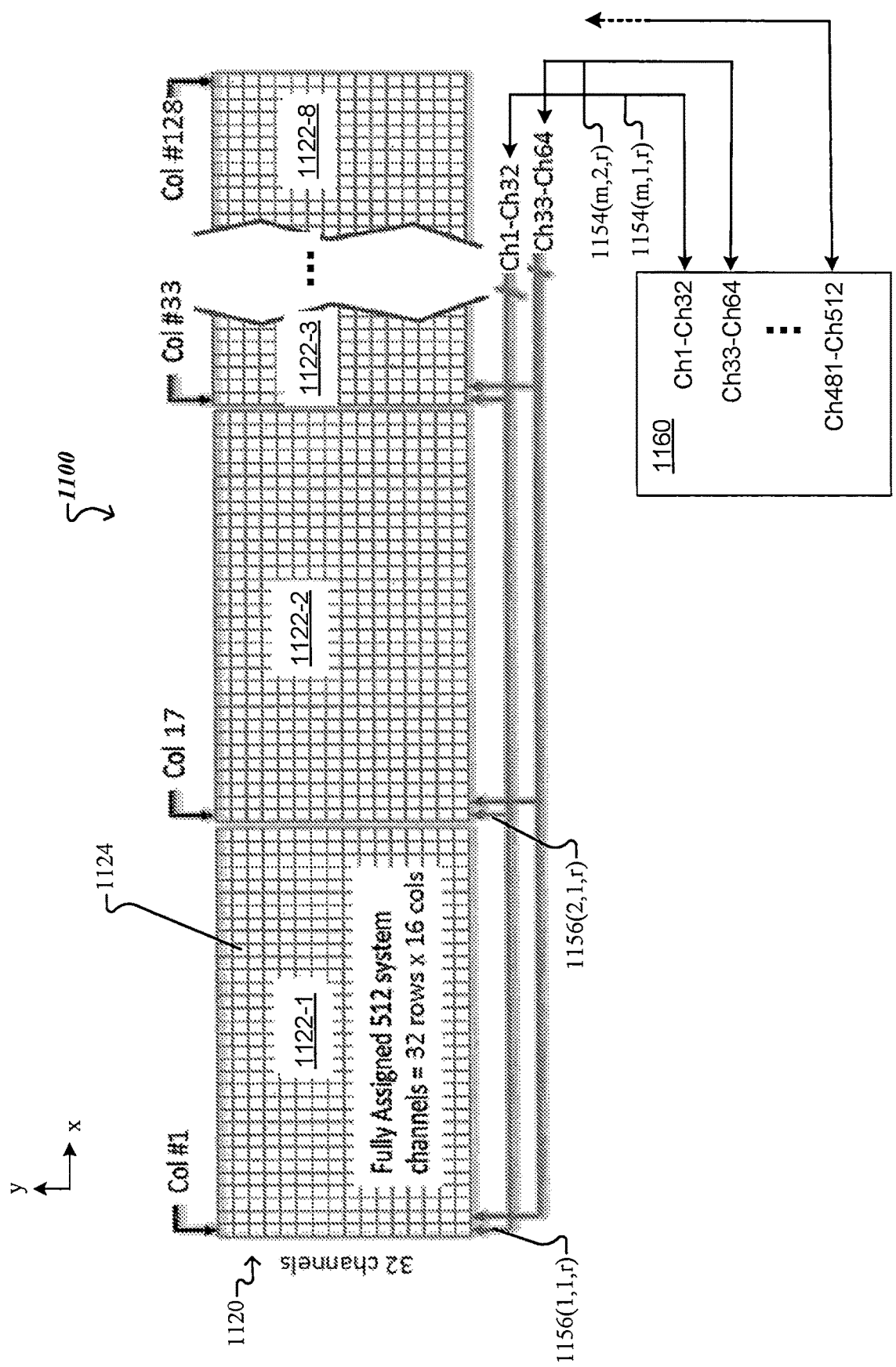
FIGS. 11-12 show aspects of examples of modular ultrasound systems that use the disclosed modular piezoelectric sensor array with co-integrated electronics and are to be coupled with an US imaging system.

The modular transducer system 100 of the transducer system 1000 can be controlled by an US imaging system to form sequences of US beams, potentially of different apertures, that can be used for linear array scanning. An architecture of an example of a modular US system 1100 is illustrated in FIG. 11. Here, the modular US system 1100 includes an array 1120 of 32×128=4096 piezoelectric elements and is comprised of M (e.g., M=8) individual transducer modules, like the transducer module 102 described above in connection with FIG. 1B, where each transducer module has a transducer matrix 1122-$k$ with 32×16=512 piezoelectric elements, where k=1 . . . M. The modular US system 1100 further includes interconnect bus lines 1154 arranged and configured to couple the transducer matrices 1122-1, . . . , 1122-M of the respective transducer modules with an US imaging system 1160. The US imaging system 1160 is configured to function as a beamforming system with, e.g., 512 channels, when the modular US system 1100 is operated in source mode, and as a 512-channel detection system, when the modular US system is operated in detector mode. The US imaging system 1100's channels are mapped to the 32×128 piezoelectric element large area array 1120 by breaking it into individual transducer matrices or banks of 16×32 uniquely assigned piezoelectric elements. A 32×16 piezoelectric element active aperture is translated across the 32×128 piezoelectric element array 1120 by selectively turning on and off successive columns of switches in neighboring banks of piezoelectric elements, {1122-$k$, 1122-($k$+1)}. As described below in connection with FIGS. 13A-13B, 14A-14B and 15A-15B, different sized active apertures can be created by trading off the number of channels corresponding to piezoelectric elements along the elevation direction with the number of channels corresponding to piezoelectric elements along the azimuthal direction by using different switch configurations.

Switches used to implement the switching configurations described below may be high voltage electrical switches, low voltage electrical switches, or micro-electro-mechanical (MEMs) switches. In some implementations, for optimal reduction in cross-talk, individual switches can be grouped in a network of three switches which all share a first terminal, and where one of the switches has its second terminal connected to ground.

Operation of the foregoing architecture is as follows: the US imaging system 1160's channels 1-32 are mapped uniquely to each element in column #1. For example, in the first bank 1122-1, the top left-most piezoelectric element is mapped to channel #1, the one below it to channel #2, etc., e.g., using interconnect bus lines 1154($m$,1,$r$). Here, the bank index "m" represents any of the M transducer matrices 1122-$k$, the column index "1" represents the first column, and the row index "r" represents any of the 32 rows of each column. The next column is mapped to channels #33-64, e.g., using interconnect bus lines 1154($m$,2,$r$). Here, the column index "2" represents the second column. In the next bank 1122-2, the same channels are again mapped uniquely as shown. Note that the interconnect bus lines 1156 can be disposed either along the azimuthal direction or the elevation direction. In some implementations, the interconnect bus lines 1156 can be disposed along both the azimuthal and elevation directions. In such cases, switches of the modular ultrasound system 1100 can be arranged and configured to selectively connect the system channels in the multi-channel processing unit 1160 to the azimuthally-oriented interconnect bus lines in a first operating mode, and to the elevationally-oriented interconnect bus lines in a second operating mode, for instance.

Each piezoelectric element 1124 can be selected using a single mux switch which can either be turned on or off. This switch is part of an ASIC associated with a respective bank 1122-$k$ of the modular US system 1100 and is configured to select that piezoelectric element for a transmit (i.e., source mode)/receive (i.e., detector mode) connection to the US imaging system 1160 or to be isolated. For instance, switches can contain locally integrated control circuits which may further be configured to switch between stored state bits one or more times during transmit and receive cycles. An example of a scanning procedure for imaging is to create a window of piezoelectric elements which translates linearly from left to right across the face of the array 1120. Such a window can be created by selecting which piezoelectric elements are connected to the US imaging system 1160's channels at any particular time.

Piezoelectric element #1 (top left-most) in bank 1122-1, and piezoelectric element #1 in bank 1122-2 are both connected to US imaging system 1160's channel #1 through their respective mux switches, e.g., using interconnect bus line combinations 1154($m,1,r$)+1156($1,1,r$) and 1154($m,1,r$)+1156($2,1,r$), respectively. Note that the interconnect bus lines are also referred to simply as channel lines. Here, the bank index "1" represents the first transducer matrix 1122-1 and the bank index "2" represents the second transducer matrix 1122-2. At the start of scanning, the mux switch in piezoelectric element #1, bank 1122-1 is turned on so that it can transmit and receive. However, the mux switch in piezoelectric element #1, bank 1122-2 is turned off. It does not transmit and does not contribute to receive beamforming.

At the next stage of scanning, the active window will shift by one column to the right. This is done by turning the switch in piezoelectric element #1, bank 1122-1 to the off state, while simultaneously turning the switch in piezoelectric element #1, bank 1122-2 to the on state. Similarly, all of the piezoelectric elements in the column below piezoelectric element #1, bank 1122-1 will turn off, and all of the piezoelectric elements in column #1, bank 1122-2 will turn on. This same procedure continues with every new shift of the active aperture until it has translated all completely across the array 1120, e.g., from bank 1122-3 through to bank 1122-8.

A second feature of the array architecture, is interconnection of piezoelectric elements within each bank 1122-$k$. In some implementations, interconnection can be provided using additional mux switches between the piezoelectric elements that connect neighbors in a given column to each other (e.g. piezoelectric element #1 connects to piezoelectric element #2 using a switch 145Y, as shown in FIG. 2) or connects neighbors in adjacent columns together (e.g. piezoelectric element #1 connects to piezoelectric element #33 in the second column using a switch 145X, as shown in FIG. 2). In some implementations, interconnection can also be provided using additional routing at the ASIC level to connect mirrored piezoelectric elements together. This takes advantage of the fact that for an array 1120 that is not steered in the elevation direction, the beamforming delays for piezoelectric elements that are equidistant relative to the horizontal midline are identical. In some implementations, interconnection can also be provided using additional routing at the ASIC level to connect mirrored piezoelectric elements together that are symmetrically situated relative to a horizontally (i.e., azimuthally) oriented midpoint to the active array aperture.

In each of these cases, the grouping of piezoelectric elements results in the freeing up of additional beamforming channels of the US imaging system 1160. These extra beamforming channels can be used to grow the width of the active aperture along the azimuthal direction, as described below.

Figure 12:
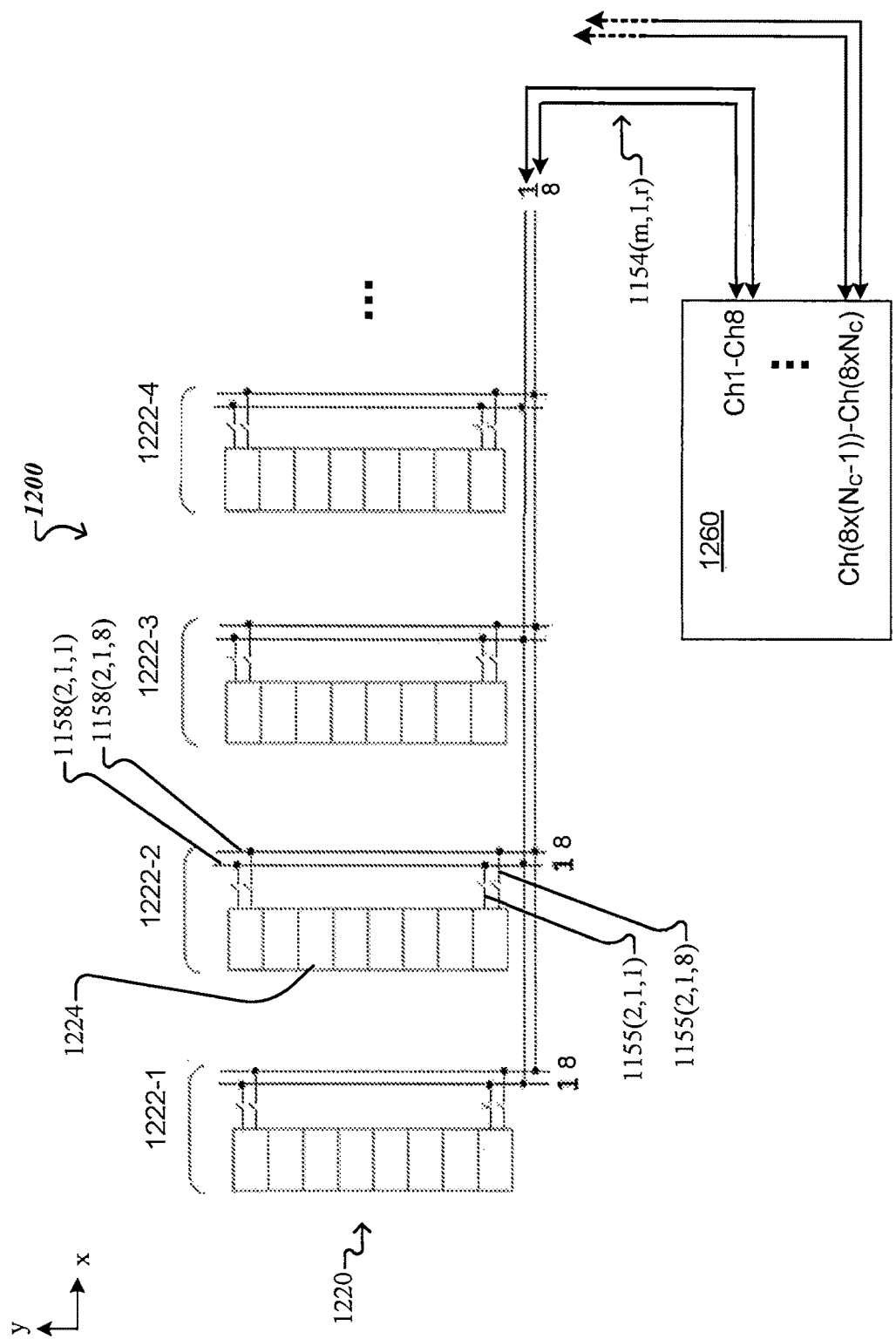

FIG. 12 illustrates an architecture of another example of a modular US system 1200. In this example, the modular US system 1200 includes an array 1220 of M×($N_R$×$N_C$) piezoelectric elements 1224 and is comprised of M individual transducer modules, like the transducer module 102 described above in connection with FIG. 1B, where $N_R$ is the number of rows (e.g., N=8), and $N_C$ is the number of columns of a transducer matrix 1222. In the example illustrated in FIG. 12, each transducer module has a transducer matrix 1222-$k$ with 8×$N_C$ piezoelectric elements, where k=1 . . . M. Only the first column of each of the first four transducer matrices 1222-1, 1222-2, 1222-3, 1222-4 are shown in FIG. 12. The modular US system 1200 further includes interconnect bus lines 1154 arranged and configured to couple the transducer matrices 1222-1, . . . , 1222-M of the respective transducer modules with an US imaging system 1260. In this example, the US imaging system 1260 has 8×$N_C$ channels mapped to the M×(8×$N_C$) piezoelectric element large area array 1220 by breaking it into individual transducer matrices or banks of 8×$N_C$ uniquely assigned piezoelectric elements. The modular US system 1200 can be operated in conjunction with the US imaging system 1260 in a manner similar to the manner of operation of modular US system 1100 in conjunction with the US imaging system 1160, as described above in connection with FIG. 11. Operation of modular US system 1200 is used to illustrate the ability to trade-off channel connections in the elevation direction and in the azimuthal direction for optimal use of array 1220's resources. As shown in FIG. 12, each piezoelectric element in each transducer matrix 1222-$k$ is connected to two different channel lines 1154($m,1,r$)+1158($m,1,r$) using two respective switches 1155($m,1,r$). This pair of switches is part of an interface unit, which may include other components, as described below. Here, the bank index "m" represents any of the M transducer matrices 1222-$k$, the column index "1" represents the first column, and the row index "r" represents any of the 8 rows of each column. A multiplicity of channel lines exist within each column, with the number of lines being equivalent to the number of elements. With this configuration, it is possible to connect the top piezoelectric element and the bottom piezoelectric element of a column together on one channel (e.g., channel 1), and more generally piezoelectric elements are paired symmetrically relative to a midline parallel to the azimuthal direction. Alternatively, it is possible to connect each piezoelectric element of a column to its own separate channel (e.g., top element to channel 1 and bottom element to channel 8).

The latter case is described below in connection with FIGS. 13A-13C. In this example, the modular US system 1200 includes eight transducer modules 1202-1, . . . , 1202-8, each transducer module having 8×16 piezoelectric elements. At $t_1$, the modular US system 1200 emits along the z-axis a first instance of US beam 1301($t_1$)—which has an aperture size $d_Y$ along the elevation direction and dx along the azimuthal direction, and a focal length f—by implementing a first coupling scheme 1300, over columns 1-16, in the following manner: each piezoelectric element 1224 of a column is connected to its own channel, e.g., the first piezoelectric element of column 1 of module 1202-1 being connected to channel 1 through an appropriate combination of channel lines 1154($m,1,r$)+1156($1,1,r$) and a switch 1155(1,1,1) to receive a first signal $S_1$; and so on, the eighth piezoelectric element of column 1 of module 1202-1 being connected to channel 8 through an appropriate combination of channel lines 1154($m,1,r$)+1156($1,1,r$) and a switch 1155(1,1,8) to receive an eighth signal $S_8$; and so on, the eighth piezoelectric element of column 16 of module 1202-1 being connected to channel 8 through an appropriate combination of channel lines 1154($m,1,r$)+1156($1,16,r$) and a switch 1155(1,16,8) to receive a 128$^{th}$ signal $S_{128}$. In this manner, the modular US system 1200 can acquire a first "line" of thickness dx of a scanned image of a target that is spaced apart at a distance f. At $t_2$, the modular US system 1200 emits along the z-axis a second instance of US beam 1301($t_2$) by implementing the first coupling scheme 1300 over columns 2-17. In this manner, the modular US system 1200 can acquire a second line of thickness dx of the scanned image of the target. And so on, at $t_{112}$, the modular US system 1200 emits along the z-axis a $112^{th}$ instance of US beam 1301($t_{112}$) by implementing the first coupling scheme 1300 over columns 113-128. In this manner, the modular US system 1200 can acquire a last (i.e., $112^{th}$) line of thickness dx of the scanned image of the target.

The case where mirrored piezoelectric elements are connected to the same channel frees up a second channel to be used elsewhere in the array 1220. This allows the size of the aperture in the azimuthal direction to be effectively doubled. This case is described below in connection with FIGS. 14A-14C. In this example, the same modular US system 1200 used in connection with FIGS. 13A-13C is being used. At $t_1$, the modular US system 1200 emits along the z-axis a first instance of US beam 1401($t_1$)—which has an aperture size $d'_Y$ along the elevation direction and $d'_X$ along the azimuthal direction (that is half $d_X$ obtained using coupling scheme 1300 which leads to an equivalent improvement in image resolution), for about the same focal length f—by implementing a second coupling scheme 1400, over columns 1-32, in the following manner: each of a pair of piezoelectric elements 1224 mirrored relative a center of a column is connected to the pair's common channel, e.g., the $1^{st}$ and $8^{th}$ piezoelectric elements of column 1 of module 1202-1 being connected to channel 1 through an appropriate combination of channel lines 1154($m,1,r$)+1156($1,1,r$) and switch 1155($1,1,1$) to each receive a $1^{st}$ signal $S_1$; and so on, the $4^{th}$ and $5^{th}$ piezoelectric elements of column 1 of module 1202-1 being connected to channel 4 through an appropriate combination of channel lines 1154($m,1,r$)+1156($1,1,r$) and switch 1155($1,1,4$) to receive a $4^{th}$ signal $S_4$; and so on, the $4^{th}$ and $5^{th}$ piezoelectric elements of column 16 of module 1202-2 being connected to channel 128 through an appropriate combination of channel lines 1154($m,1,r$)+1156($1,16,r$) and switch 1155($2,16,4$) to receive a $128^{th}$ signal $S_{128}$. In this manner, the modular US system 1200 can acquire a first "line" of thickness $d'_X$ of a scanned image of a target that is spaced apart at a distance f. At $t_2$, the modular US system 1200 emits along the z-axis a second instance of US beam 1401($t_2$) by implementing the second coupling scheme 1400 over columns 2-33. In this manner, the modular US system 1200 can acquire a second line of thickness $d'_X$ of the scanned image of the target. And so on, at $t_{96}$, the modular US system 1200 emits along the z-axis a $96^{th}$ instance of US beam 1401($t_{96}$) by implementing the second coupling scheme 1400 over columns 97-128. In this manner, the modular US system 1200 can acquire a last (i.e., $96^{th}$) line of thickness $d'_X$ of the scanned image of the target.

Note that it is possible to focus at a desired focal depth, f, by adding electronic delays on the different piezoelectric elements/channels. This can be done both on transmit mode and receive mode. On transmit mode this can be done at a single focal depth (or in some cases a small number of depths), and on receive mode it is done continuously with very fine resolution.

The coupling scheme 1400, described above in connection with FIGS. 14A-14C, is based on connecting mirrored piezoelectric elements to gain larger aperture, and improve image acquisition. A further grouping is possible between adjacent piezoelectric elements by integrating switches between adjacent piezoelectric elements themselves. This grouping can be done either horizontally (i.e., between piezoelectric elements of adjacent columns, using switches 145X, as shown in FIG. 2) or vertically (i.e., between piezoelectric elements of adjacent rows, using switches 1145Y, as shown in FIG. 15A) or both. The combined groupings of adjacent piezoelectric elements as well as mirrored piezoelectric elements allow the aperture to be spread across four modules as illustrated in FIGS. 15A-15C.

In this example, the same modular US system 1200 used in connection with FIGS. 13A-13C is being used. At $t_1$, the modular US system 1200 emits along the z-axis a first instance of US beam 1501($t_1$)—which has an aperture size $d''_Y$ along the elevation direction and $d''_X$ along the azimuthal direction (that is four times smaller than dx obtained using coupling scheme 1300 which leads to an equivalent improvement in image resolution), for about the same focal length f—by implementing a third coupling scheme 1500, over columns 1-64, in the following manner: One of each pair of adjacent ones of a set of four piezoelectric elements 1224 that is mirrored relative a center of a column is connected to the pair's common channel and to its adjacent piezoelectric element, e.g., the $1^{st}$ and $8^{th}$ piezoelectric elements of column 1 of module 1202-1 being connected to channel 1 through an appropriate combination of channel lines 1154($m,1,r$)+1156($1,1,r$) and switch 1155($1,1,1$), the $1^{st}$ and $2^{nd}$ piezoelectric elements being connected to each other through switch 1145Y($1,2$) and the $7^{th}$ and $8^{th}$ piezoelectric elements being connected to each other through switch 1145Y($7,8$), such that each receives a $1^{st}$ signal $S_1$; the $3^{rd}$ and $6^{th}$ piezoelectric elements of column 1 of module 1202-1 being connected to channel 3 through an appropriate combination of channel lines 1154($m,1,r$)+1156($1,1,r$) and switch 1155($1,1,3$), the $3^{rd}$ and $4^{th}$ piezoelectric elements being connected to each other through switch 1145Y($3,4$) and the $5^{th}$ and $6^{th}$ piezoelectric elements being connected to each other through switch 1145Y($5,6$), such that each receives a $3^{rd}$ signal $S_3$; and so on, the $2^{nd}$ and $7^{th}$ piezoelectric elements of column 16 of module 1202-4 being connected to channel 127 through an appropriate combination of channel lines 1154($m,1,r$)+1156($1,1,r$) and switch 1155($4,16,2$), the $1^{st}$ and $2^{nd}$ piezoelectric elements being connected to each other through switch 1145Y($1,2$) and the $7^{th}$ and $8^{th}$ piezoelectric elements being connected to each other through switch 1145Y($7,8$), such that each receives a $127'$ signal $S_{127}$; and the $4^{th}$ and $5^{th}$ piezoelectric elements of column 16 of module 1202-4 being connected to channel 4 through an appropriate combination of channel lines 1154($m,1,r$)+1156($1,1,r$) and switch 1155($4,16,4$), the $3^{rd}$ and $4^{th}$ piezoelectric elements being connected to each other through switch 1145Y($3,4$) and the $5^{th}$ and $6^{th}$ piezoelectric elements being connected to each other through switch 1145Y($5,6$), such that each receives a $128^{th}$ signal $S_{128}$. In this manner, the modular US system 1200 can acquire a first "line" of thickness $d''_X$ of a scanned image of a target that is spaced apart at a distance f. At $t_2$, the modular US system 1200 emits along the z-axis a second instance of US beam 1501($t_2$) by implementing the third coupling scheme 1500 over columns 2-65. In this manner, the modular US system 1200 can acquire a second line of thickness $d''_X$ of the scanned image of the target. And so on, at $t_{64}$, the modular US system 1200 emits along the z-axis a $64^{th}$ instance of US beam 1401($t_{64}$) by implementing the third coupling scheme 1500 over columns 65-128. In this manner, the modular US system 1200 can acquire a last (i.e., $64^{th}$) line of thickness $d''_X$ of the scanned image of the target.

The third coupling scheme 1500, described above in connection with FIGS. 15A-15C, is based on combining mirrored and double groupings to facilitate higher resolution than the ones obtained based on coupling schemes 1300 and 1400. Such a "high resolution mode" can be used in conjunction with a high frame rate "survey" mode in the following manner. The survey mode can be implemented when adjacent piezoelectric elements 1224 are coupled, not along the elevation direction (as in coupling schemes 1400 and 1500), but along the azimuthal direction, e.g., using switches 145X(j,k;j+1,k), described in FIG. 2, which directly couple, in this example the $k^{th}$ piezoelectric element from column j to the $k^{th}$ piezoelectric element from adjacent column j+1. Using this coupling scheme, the azimuthal pitch will be double the azimuthal pitch of the coupling schemes 1400, 1500. So in this case, the array 1220 can be scanned at twice the rate, of course with half (2× worse) resolution. This implements a high frame rate survey mode which can be useful for quickly obtaining a low resolution image of a large target region, which can be implemented prior to a high resolution mode (e.g., based on coupling scheme 1500) for obtaining a zoomed-in, detailed image of a portion of interest of the target region, where the portion of interest has been identified in the low resolution image.

The array 1220 can be programmed with a completely new configuration (e.g., 1300, 1400, 1500 or other configurations) on every transmit/receive cycle. In this way the array 1220 can operate for example as a first window of $N_C×2$ piezoelectric elements on transmit/receive cycle 1, and then operate as a completely addressed second $N_C$ column×8 row window at the center of the array on transmit/receive cycle 2.

The advantage of this highly flexible approach is that it provides near transparent access to the individual 2D piezoelectric elements 1224 of the array 1220 in order to enable novel beamforming algorithms which, for example, could be used for improving image quality in the presence of acoustic aberration or for deep imaging at higher resolution.

Within the architectures described above in connection with FIGS. 11 and 12, the ASICs integrated within each of the modular US systems 1100 and 1200 can provide buffering of the signals from each piezoelectric element 1124 or 1224. These buffers are part of respective interface units, along with switches 1155, and are disposed between the piezoelectric elements and their respective switches. It is therefore possible to sum the signals of multiple piezoelectric elements by connecting them through their switches 1155 to an operational amplifier located outside the modular US systems 1100 and 1200 with a resistor feedback. The switch on resistances operates with the amplifier and its feedback resistor to form an analog summing operation for signals detected by the piezoelectric elements. This operation can be used to implement the groupings described above during the receive cycle.

Multiple frequencies and array pitches of $\lambda/4$, $\lambda/2$ and $\lambda$ are supported in the architecture described above in connection with FIGS. 13B-13C, 14B-14C and 15B-15C by grouping neighboring piezoelectric elements according to their respective operating frequencies. For example, four piezoelectric elements at a pitch $\lambda/2$ can be grouped to form a single large "piezoelectric element" at a pitch $\lambda$. This grouping over the entire array 1220 can be used to expand the array aperture to cover a larger area in order to realize finer resolution at the given operating frequency.

Thus, particular embodiments of the invention have been described. Other embodiments are within the scope of the following claims.

What is claimed is:

1. A modular array comprising:
    one or more array modules, wherein each array module includes
    one or more transducer arrays, wherein each of the one or more transducer arrays comprises a plurality of piezoelectric elements;
    a conducting interposer arranged and configured to provide acoustic absorbing backing for the one or more transducer arrays; and
    one or more Application Specific Integrated Circuits (ASICs);
    wherein the conducting interposer and the one or more ASICs are in electrical contact with each other at a first direct electrical interface;
    wherein the conducting interposer and the one or more transducer arrays are in electrical contact with each other at a second direct electrical interface; and
    wherein a height of the conducting interposer is between $5\lambda$ and $20\lambda$, and $\lambda$, is a wavelength of an ultrasound beam emitted by the modular array.

2. The modular array of claim 1, wherein a width of the modular array along an azimuthal direction and a height of the modular array along an elevation direction are roughly equal.

3. The modular array of claim 1, wherein a width of the modular array along an azimuthal direction is greater than two times a height of the modular array along an elevation direction.

4. The modular array of claim 1, wherein pitches of the conducting interposer along azimuthal and elevation directions match respective pitches of a transducer array of the one or more transducer arrays.

5. The modular array of claim 1, wherein the plurality of piezoelectric elements comprises
    a composite of PMN-PT or PIN-PMN-PT piezoelectric material, and insulating filler material.

6. The modular array of claim 5, wherein
    the insulating filler material comprises a non-conducting epoxy, and the non-conducting epoxy includes one or more of a plasticizer, or scattering balloons.

7. The modular array of claim 1, wherein at least one of the one or more transducer arrays comprises multiple acoustic matching layers.

8. The modular array of claim 1, wherein the conducting interposer comprises an electrically insulating grid frame with holes, and
    a conducting material that is acoustically attenuating and fills the holes of the electrically insulating grid frame.

9. The modular array of claim 8, wherein a width along an elevation direction and a width along an azimuthal direction of the conducting material within the holes are each at least 90% of respective pitches of a transducer array of the one or more transducer arrays.

10. The modular array of claim 8, wherein
    the electrically insulating grid frame comprises a non-conducting material that is configured to suppress transmission of lateral acoustic modes.

11. The modular array of claim 10, wherein the non-conducting material
    comprises one or more of a solid epoxy, an epoxy with a plasticizer, or an epoxy with scattering balloons.

12. The modular array of claim 10, wherein the conducting material has a same acoustic impedance as the non-conducting material.

13. The modular array of claim 8, wherein the conducting material comprises scattering balloons.

14. The modular array of claim 8, wherein the first direct electrical interface comprises a silver loaded epoxy that is plated with a layer of nickel and a layer of gold.

15. The modular array of claim 14, wherein the layer of nickel is plated with a layer of palladium.

16. The modular array of claim 1, wherein the first direct electrical interface comprises a laminated layer of copper that is plated with a layer of nickel and a layer of gold.

17. The modular array of claim 1, wherein a surface of the conducting interposer adjacent the first direct electrical interface comprises a crossing pattern of slots that are filled by silver loaded epoxy.

18. The modular array of claim 1, wherein the height of the conducting interposer is uniform.

19. The modular array of claim 1, wherein the height of the conducting interposer is realized by stacking a plurality of thinner conducting interposers.

20. The modular array of claim 1, further comprising:
support structures that respectively support the each of one or more transducer arrays and
a gimbal system mechanically coupled to the support structures and configured to cause,
when actuated, changes in position and orientation of the each of one or more transducer arrays.

* * * * *

UNITED STATES PATENT AND TRADEMARK OFFICE
CERTIFICATE OF CORRECTION

| | |
|---|---|
| PATENT NO. | : 11,134,918 B2 |
| APPLICATION NO. | : 15/999109 |
| DATED | : October 5, 2021 |
| INVENTOR(S) | : Robert G. Wodnicki et al. |

It is certified that error appears in the above-identified patent and that said Letters Patent is hereby corrected as shown below:

In the Specification

Replace the paragraph in Column 1, Lines 21-24, with the following paragraph:
--This invention was made with government support under Contract Nos. P41 RR011795, DK055274, P41 EB002182, and CA199658 awarded by the National Institutes of Health (NIH). The Government has certain rights in this invention.--

Signed and Sealed this
Eighteenth Day of July, 2023

*Katherine Kelly Vidal*

Katherine Kelly Vidal
*Director of the United States Patent and Trademark Office*